(12) United States Patent
Bouchard

(10) Patent No.: US 12,350,201 B2
(45) Date of Patent: Jul. 8, 2025

(54) MOUNTING APPARATUS FOR SECURING EQUIPMENT TO A PATIENT TRANSPORT SYSTEM

(71) Applicant: TECHNOLOGIES CGC INC., Quebec (CA)

(72) Inventor: Carl Bouchard, Quebec (CA)

(73) Assignee: TECHNOLOGIES CGC INC., Quebec (CA)

( * ) Notice: Subject to any disclaimer, the term of this patent is extended or adjusted under 35 U.S.C. 154(b) by 0 days.

(21) Appl. No.: 17/769,158

(22) PCT Filed: Oct. 16, 2020

(86) PCT No.: PCT/CA2020/051392
§ 371 (c)(1),
(2) Date: Apr. 14, 2022

(87) PCT Pub. No.: WO2021/072549
PCT Pub. Date: Apr. 22, 2021

(65) Prior Publication Data
US 2024/0108519 A1    Apr. 4, 2024

Related U.S. Application Data

(60) Provisional application No. 62/915,806, filed on Oct. 16, 2019.

(51) Int. Cl.
*A61G 1/04* (2006.01)
*A61G 1/00* (2006.01)
(Continued)

(52) U.S. Cl.
CPC ............... *A61G 1/04* (2013.01); *A61G 7/05* (2013.01); *A61G 13/101* (2013.01);
(Continued)

(58) Field of Classification Search
CPC .......... A61G 1/04; A61G 1/00; A61G 13/101; A61G 2203/78; A61G 3/00; A61G 7/05;
(Continued)

(56) References Cited

U.S. PATENT DOCUMENTS 4,511,158 A     4/1985   Varga et al.
5,152,486 A  *  10/1992  Kabanek ................ A61B 90/60
                                                      5/507.1
(Continued)

FOREIGN PATENT DOCUMENTS

DE      102017110001 A1    11/2018
WO    WO-2016179444 A1  *  11/2016   ............... A61G 1/04

OTHER PUBLICATIONS

"Pivot." Collins Dictionary, www.collinsdictionary.com/us/dictionary/english/pivot.*

(Continued)

*Primary Examiner* — Madison Emanski
(74) *Attorney, Agent, or Firm* — BCF LLP

(57) ABSTRACT

A mounting apparatus for moveably securing equipment to a patient transport system, the mounting apparatus comprising: a first arm having a proximal end, a distal end and a longitudinal axis, and configured to support equipment; and a clamping system attachable to the patient transport system and configured to receive the proximal end of the first arm for removeably attaching the first arm to the patient transport system and for allowing a rotation of the first arm relative to the patient transport system between an upright position and a reclined position.

16 Claims, 18 Drawing Sheets

(51) Int. Cl.
*F16M 11/04* (2006.01)
*F16M 11/24* (2006.01)
*F16M 13/02* (2006.01)

(52) U.S. Cl.
CPC ........ *A61M 5/1415* (2013.01); *F16M 11/041* (2013.01); *F16M 11/24* (2013.01); *F16M 13/02* (2013.01); *F16M 13/022* (2013.01); *A61G 1/00* (2013.01); *A61G 2203/78* (2013.01); *A61M 5/1417* (2013.01)

(58) Field of Classification Search
CPC ...... A61G 2203/20; A61G 13/10; A61G 5/10; A61G 7/0503; A61G 12/008; F16M 11/041; F16M 13/02; F16M 13/022; F16M 11/08; F16M 11/24; F16M 11/10; F16M 11/2014; F16M 2200/024; F16M 11/18; F16M 13/00; F16M 11/046; B60P 7/0815; A61M 5/1415; A61M 5/1417; A61M 5/1413; F16B 2/10; F16B 2/185; A61B 50/10; A61B 50/20
USPC ................ 5/507.1, 658, 503.1, 600; 108/49; 248/121, 124.1, 125.1, 230.1, 223.41
See application file for complete search history.

(56) References Cited

U.S. PATENT DOCUMENTS

| | | | |
|---|---|---|---|
| 5,362,021 A * | 11/1994 | Phillips | A61G 13/101 5/507.1 |
| 9,746,125 B2 * | 8/2017 | Bowman | F16M 11/125 |
| 11,007,951 B1 | 5/2021 | Zarecky | |
| 2002/0011543 A1 * | 1/2002 | Chinn | A61M 5/1415 248/125.1 |
| 2003/0046764 A1 | 3/2003 | Smeed | |
| 2005/0223494 A1 | 10/2005 | Ambrose et al. | |
| 2006/0255220 A1 * | 11/2006 | Skripps | A61G 13/04 248/228.4 |
| 2007/0252068 A1 * | 11/2007 | Secora | F16M 11/2085 248/458 |
| 2008/0217910 A1 | 9/2008 | Walke | |
| 2011/0121149 A1 | 5/2011 | Herskovic | |
| 2012/0262039 A1 | 10/2012 | Daugbjerg et al. | |
| 2014/0374564 A1 | 12/2014 | Schroeder et al. | |
| 2014/0374565 A1 | 12/2014 | Tan | |
| 2015/0041419 A1 | 2/2015 | Hasegawa | |
| 2015/0090849 A1 | 4/2015 | Breitweiser et al. | |
| 2015/0273138 A1 | 10/2015 | Wolff et al. | |
| 2016/0031382 A1 | 2/2016 | Chinn et al. | |
| 2016/0324701 A1 * | 11/2016 | Cambridge | F16B 2/185 |
| 2017/0209318 A1 | 7/2017 | Schroeder et al. | |

OTHER PUBLICATIONS

"Rim." Cambridge Dictionary, https://dictionary.cambridge.org/dictionary/english/rim.*
International Search Report of International Application No. PCT/CA2020/051392; Search issued on Dec. 7, 2020, Authorized Officer: Branka Ristovski, 3 pages.
European Search Report issued in co-pending European patent application No. 20877841.5 on Sep. 18, 2023.

* cited by examiner

MOUNTING APPARATUS FOR SECURING EQUIPMENT TO A PATIENT TRANSPORT SYSTEM

FIELD OF THE DISCLOSURE

The present disclosure relates to a mounting apparatus for securing equipment to a patient transport system, such as, but not limited to personal transportation systems such as stretchers, wheelchairs or portable beds.

BACKGROUND OF THE DISCLOSURE

Patient transportation systems include, for example, stretchers, wheelchairs and portable beds. Oftentimes, along with transporting the patient, there is often a need to transport equipment associated with the patient.

A number of factors must be taken into account when such equipment includes medical equipment relating to the patient. Medical equipment must be secured during transportation to prevent injuries as well as damage to the equipment. Medical equipment can be heavy and cumbersome and often lack handles for ease of transportation. The manner of securing the equipment must not restrict access to either the equipment or the patient, and should allow the medical equipment to be installed and removed easily.

Current solutions for mounting medical equipment to patient transportation systems include attaching the medical equipment near the patient with straps or seat belts. The medical equipment is also sometimes placed on the patients themselves.

However, these current solutions are far from ideal. They do not secure the medical equipment in a manner which allows for secure restraint, ease of access, as well as quick and easy release. They also do not take into account the cumulative weight of the equipment.

Furthermore, certain existing solutions are not able to be used with different medical devices from a multitude of companies, and tend to be adapted for use to a particular equipment.

Therefore, there is a need for mounting apparatus which overcome or reduce at least some of the above-described problems.

SUMMARY OF THE DISCLOSURE

Broadly, there is provided mounting apparatus for moveably securing equipment to a patient transport system.

From a first aspect, there is provided a mounting apparatus for moveably securing equipment to a patient transport system, the mounting apparatus comprising: a first arm having a proximal end, a distal end and a longitudinal axis, and configured to support equipment; and a clamping system attachable to the patient transport system and configured to receive the proximal end of the first arm for removeably attaching the first arm to the patient transport system and for allowing a rotation of the first arm relative to the patient transport system between an upright position and a reclined position.

In certain embodiments, the clamping system comprises a body having a slot defined therein for receiving the proximal end of the first arm, and a removable pivot pin, insertable through the body and the proximal end of the first arm.

In certain embodiments, the body comprises a foot portion and a cover portion, the foot portion configured to be attached to the patient transport system, and the cover portion arranged to be removeably attached to the foot portion, the slot being defined between the foot and cover portions.

In certain embodiments, there is an opening defined in the proximal end of the first arm configured such that the pivot pin can extend therethrough.

In certain embodiments, the mounting apparatus further comprises interengageble elements between a rim of the proximal end of the first arm and a wall inside the body, the wall at least partially defining the slot.

In certain embodiments, the interengageable elements comprise teeth and notches, the teeth extending from the rim and the notches being formed in the wall.

In certain embodiments, the proximal end is a flat end having two faces and the rim separating the two faces.

In certain embodiments, the clamping system further comprises a pin extendable through the body, transverse to the pivot pin when assembled, and selectively engageable with a first opening and/or a second opening in the proximal end of the first arm to lock the first arm in the upright position and/or reclined position, respectively. In certain embodiments, the pin is resiliently biased towards the first arm. In certain embodiments, the first opening and the second opening are spaced from one another on the rim of the proximal end of the first arm.

In certain embodiments, the mounting apparatus further comprises a second arm spaced from the first arm and connected thereto by a connecting member at respective distal ends of each of the first arm and the second arm, the second arm having a distal end, a proximal end and a longitudinal axis.

In certain embodiments, the mounting apparatus further comprises a platform at the distal ends of the first arm and the second arm, the platform having a support face with a support surface plane which is substantially transverse to the longitudinal axis of the first arm and the second arm.

In certain embodiments, the platform is positioned distally of the connecting member and connected thereto.

In certain embodiments, the mounting apparatus further comprises at least one transverse reinforcement member extending along at least a portion of the platform, the at least one reinforcement member extending substantially transversely to the connecting member.

In certain embodiments, the mounting apparatus further comprises at least one handle extending from the first arm and/or the second arm.

In certain embodiments, the patient transport system is a personal transport system such as a stretcher. In certain embodiments, the equipment is medical equipment.

In certain embodiments, the mounting apparatus further comprises at least a portion of a coupling device attached to the frame, the at least a portion of the coupling device configured to be releasably attached to the equipment.

In certain embodiments, the coupling device comprises a base member and a release member releasably connectable together, the base member being connectable to the frame of the mounting apparatus and the release member being connectable to the equipment.

In certain embodiments, the base member has a front face including a contact portion for contacting a contact face of the release member; the release member comprises a body, at least a portion of the body being configured to be received in a pocket on the front face of the base member when the base member and the release member are in the coupled position, the pocket having an open access end through which the release member can be slidingly inserted and removed; a stop member moveable, by an actuator, between a lock position in which the stop member interengages with the release member to prevent removal of the release member from the pocket of the base member, and a release position in which the release member can be separated from the base member.

In certain embodiments, the base member has a shoulder extending around the contact portion to define the pocket for receiving the release member, the shoulder engageable with a portion of a flange of the release member when the release member is positioned on the base member.

In certain embodiments, the stop member is positioned in a recess within the contact portion and moveable by the actuator which is connected to a resilient lock mechanism between the lock position in which at least a portion of the stop member extends from the recess and abuts an edge of an opening defined in the release member contact face in the coupled position, and a release position in which the stop member is retracted into the recess.

In certain embodiments, the stop member has a wedge shaped portion with a thinner end of the wedge facing the open access end of the pocket, and wherein the resilient lock mechanism is configured to permit the stop member to move into the recess as the release member is slid into the pocket.

In certain embodiments, the actuator has a neutral position and a deployed position, wherein when the actuator is in the neutral position, the stop member is resiliently biased towards the lock position.

In certain embodiments, the base member comprises a plurality of spring loaded ball bearings partially extending from recesses formed in the front face of the base member and engageable with corresponding recesses defined in the contact face of the release member.

In certain embodiments, the contact face of the release member has an anti-friction layer.

In certain embodiments, the coupling device further comprises a damping member attachable to a back face of the base member and arranged to be positioned between the base member and the frame in use, the damping member being arranged to absorb vibration and/or shock.

In certain embodiments, the coupling device further comprises a top plate attachable to a collar of the release member and attachable to the equipment.

In certain embodiments, a perimeter of the body of the release member is circular in shape, such that the release member can be rotated within the pocket in one or both of the lock position and the release position when the base member is coupled to the release member. The stop member may function as a rotation point and is positioned substantially centrally of the contact portion of the base member.

In certain embodiments, a perimeter of the body of the release member has an eccentric shape such that the release member is not rotatable in the pocket of the base member when the base member is coupled to the release member.

In certain embodiments, the shoulder is configured to delimit movement of the release member orthogonally away from the front face of the base member, when the base member and the release member are in the coupled position.

From another aspect, there is provided a mounting apparatus for securing equipment to a patient transport system, the mounting apparatus comprising: a frame having a first arm spaced from a second arm and connected thereto by a connecting member at respective distal ends of each of the first arm and the second arm; a clamping system at respective proximal ends of each of the first arm and the second arm for removeably attaching the frame to the patient transport system and for allowing a rotation of the frame relative to the patient transport system between an upright position and a reclined position.

In certain embodiments, the mounting apparatus comprises a platform at the distal ends of the first arm and the second arm, the platform having a support face with a support surface plane which is substantially transverse to a longitudinal axis of the first arm and the second arm.

In certain embodiments, the platform is positioned distally of the connecting member and connected thereto.

In certain embodiments, the frame has a first side which faces the patient transport system when the frame is in the upright position, and a second side which faces away from the patient transport system, the platform extending transversely away from the first arm and the second arm on the first side.

In certain embodiments, the mounting apparatus further comprises at least one transverse reinforcement member extending along at least a portion of the platform, the at least one reinforcement member extending substantially transverse to the connecting member.

In certain embodiments, the mounting apparatus further comprises at least one handle extending from the frame.

In certain embodiments, the at least one handle is on the first side of the frame.

In certain embodiments, the at least one handle is attached to, and extends from, at least one of the first arm and the second arm.

In certain embodiments, the clamping system comprises a foot portion and a cover portion, the foot portion configured to be attached to a part of the patient transport system, and the cover portion arranged to be removeably attached to the foot portion.

In certain embodiments, the proximal end of each one of the first arm and the second arm is arranged to rotate in the respective clamping system to move the frame between the upright position and the reclined position.

In certain embodiments, the proximal end comprises a flat end having two sides and a rim with teeth extending therefrom, the teeth receivable within notches defined in the clamping system.

In certain embodiments, the mounting apparatus further comprises a first opening formed in the rim at proximal end and engageable with a resiliently biased pin extending through the foot portion, the first opening positioned such that the first opening and the pin are engaged when the frame is in the upright position.

In certain embodiments, the mounting apparatus further comprises a second opening formed in the rim at the proximal end and engageable with the resiliently biased pin, the second opening positioned such that the second opening and the pin are engaged when the frame is in the reclined position.

In certain embodiments, the flat end has an elongate opening defined therein corresponding in position with two openings defined in the cover portion when the cover portion and the foot portion are assembled.

In certain embodiments, the mounting apparatus further comprises a pivot pin receivable in at least one of the two openings of the cover portion and the elongate opening of the flat end.

In certain embodiments, the patient transport system is a personal transport system such as a stretcher.

In certain embodiments, the equipment is medical equipment.

In certain embodiments, the mounting apparatus further comprise at least one coupling device attached to the frame, the at least one coupling device configured to be releasably attached to the equipment.

In certain embodiments, the mounting apparatus further comprises at least one base member of a coupling device attached to the frame, the at least one base member releasably attachable to a release member in a coupled position, the release member being attachable to the equipment.

From another aspect, there is provided a mounting apparatus as described herein, wherein the release member comprises a plate-like body with a first side, the first side defining a planar contact face, and a second side having a collar extending therefrom, the collar positioned inwardly of a perimeter of the release member to define a flange portion; the base member having: a front face including a planar contact portion for contacting the contact face of the release member; a shoulder extending around a portion of a periphery of the planar portion to define a pocket for receiving the release member, the shoulder engageable with a portion of the flange of the release member when the release member is positioned on the base member; an open access end through which the release member can be slidingly inserted and removed from the pocket; a stop member positioned in a recess within the planar contact portion and moveable by a resilient lock mechanism and an actuator between a lock position in which at least a portion of the stop member extends from the recess and abuts an edge of an opening defined in the release member contact face in the coupled position, and a release position in which the stop member is retracted into the recess; the actuator having a neutral position and a deployed position, wherein when the actuator is in the neutral position, the stop member is resiliently biased towards the lock position.

In certain embodiments, the base member comprises a plurality of spring loaded ball bearings partially extending from recesses formed in the front face of the base member and engageable with corresponding recesses defined in the planar contact face of the release member.

In certain embodiments, the planar contact face of the release member has an anti-friction layer.

In certain embodiments, the mounting apparatus further comprises a damping member attachable to a back face of the base member and arranged to be positioned between the base portion and the frame in use, the damping member being arranged to absorb vibration and/or shock.

In certain embodiments, the mounting apparatus further comprises a top plate attachable to the collar of the release member and attachable to the equipment.

In certain embodiments, the perimeter of the plate-like body of the release member is circular in shape, the stop member of the base member is positioned substantially centrally of the planar contact portion, and the opening of the release member is positioned substantially centrally of the plate-like body, such that the release member can be rotated within the pocket when the stop member is in the lock position.

In certain embodiments, the perimeter of the plate-like body of the release member has an eccentric shape such that the release member is not rotatable in the pocket of the base member.

In certain embodiments, the equipment is medical equipment which is fragile, heavy, expensive, and may be critical for sustaining or saving the life of the patient. Therefore, ifs safe transportation and proximity to the patient is important. In certain embodiments, the patient transportation system is a personal system such as a stretcher, a wheelchair or a bed.

In certain embodiments, the mounting apparatus further comprises a securing apparatus for releasably securing the equipment to the coupling device, the securing apparatus comprising at least one support member attachable to the equipment and to the coupling device.

In certain embodiments, the support member is a base support member for supporting a base of the equipment.

In certain embodiments, the base support member comprises a plate having raised portions along at least a portion of a perimeter of the plate.

In certain embodiments, the support member comprises a backing support member for supporting a back of the equipment, wherein the backing support member comprises a pair of struts extending upwardly from the base support member.

In certain embodiments, the backing support member includes the coupling device, as defined above, attached thereto for releasably attaching the equipment.

In certain embodiments, the support member further comprises a top restraining member for engaging a top face of the equipment and extending across a top of the equipment in use, the top restraining member comprising two arms, each arm having a proximal end pivotally attached to a top end of the backing support member, the arms being pivotable between a restraining position in which they extend across the top of the equipment, and a release position in which they extend upwardly from the backing support member; further comprising a locking mechanism for locking the arms in one or both of the restraining position and the release position.

In certain embodiments, each arm has a distal end having a claw extending along a portion of a front face of the mobile equipment.

In certain embodiments, the locking mechanism comprises a spring and a pin and an unlocking bar at the proximal end of the elongate members, wherein pulling on the unlocking bar causes the locking mechanism to unlock and permit movement between the two positions.

In certain embodiments, the securing apparatus further comprises at least one clamp attached to the support member for releasably attaching the support member to the support surface.

In certain embodiments, the clamp comprises a main body, a clamping screw, a handle, a movable jaw and a disengagement mechanism to release the clamping screw, the disengagement mechanism comprising a slider moveable by a button and in engagement with the clamping screw; and a cam having a thread engageable with a thread of the clamping screw and pivotable relative to the clamping screw to engage and disengage the threads of the clamping screw by modulation of the button.

In certain embodiments, the handle is a torque handle.

In certain embodiments, the securing apparatus further comprises at least one hook attached to the support member for releasably attaching the support member to the support surface.

In certain embodiments, the at least one hook has a free end and a pivot end to which it is attached to the support member, and is moveable by the pivot end between a deployed position in which the free end extends away from the support plate, and a retracted position in which the at least one hook lies against the support member or another hook.

In certain embodiments, there are at least two hooks, spaced from one another, the at least two hooks being resiliently biased to the retracted position in which they are arranged to overlap one another.

In certain embodiments, the securing apparatus further comprises an IV pole mounting member, for mounting an IV pole in a substantially vertical position.

In certain embodiments, the securing apparatus further comprises an IV pole locking mechanism comprising a locking plate having a rod lock slot, through which an end of the IV pole is extended, and a spring resiliently biasing the plate away from the securing apparatus.

In certain embodiments, the securing apparatus further comprises an IV pole retaining member attached to the support member and arranged to receive and secure an IV pole in a horizontal storage position whilst not in use.

From another aspect, there is provided a securing apparatus for releasably securing the equipment to the mounting apparatus, the securing apparatus comprising: three support members for supporting a mobile equipment, the three support members comprising: a base support member for supporting a base of the mobile equipment, a backing support member for supporting a back of the mobile equipment, and a top restraining member for engaging a top face of the mobile equipment and extending across a top of the mobile equipment in use; and a at least a portion of a coupling device comprising a base member connectable to the mounting apparatus, and a release member connectable to one of the support members, the base member and the release member being releasably connectable together in a coupled position. In certain embodiments, the coupling device is as defined herein.

Embodiments of the mounting apparatus provide a secure manner of transporting equipment with the patient transportation. Movement of the frame between the upright position and the reclined position can allow access to the patient in the patient transportation system.

The equipment can remain secured to the frame during high acceleration and deceleration events, as well as travel on uneven surfaces. In certain embodiments, the frame can withstand impacts of up to 30 G.

Embodiments of the coupling device enable the securing and the release of the equipment by a single person, and may not require more than one hand. Embodiments of the coupling device enable the securing of mobile equipment of different sizes, shapes and configurations to the frame.

Embodiments of the coupling device enable the equipment to be easily secured to, and removed from, the frame by a sliding action to couple the base member and the release member of the coupling device. Release of the equipment from the frame can be achieved by a single push/pull button. Rotation of the equipment whilst the equipment is retained on the frame is possible in certain embodiments of the coupling device that permit rotation.

Definitions

It must be noted that, as used in this specification and the appended claims, the singular form "a", "an" and "the" include plural referents unless the context clearly dictates otherwise.

As used herein, the term "about" in the context of a given value or range refers to a value or range that is within 20%, preferably within 10%, and more preferably within 5% of the given value or range.

As used herein, the term "and/or" is to be taken as specific disclosure of each of the two specified features or components with or without the other. For example "A and/or B" is to be taken as specific disclosure of each of (i) A, (ii) B and (iii) A and B, just as if each is set out individually herein.

BRIEF DESCRIPTION OF DRAWINGS

Further aspects and advantages of the present invention will become better understood with reference to the description in association with the following in which.

DETAILED DESCRIPTION

Figure 1:
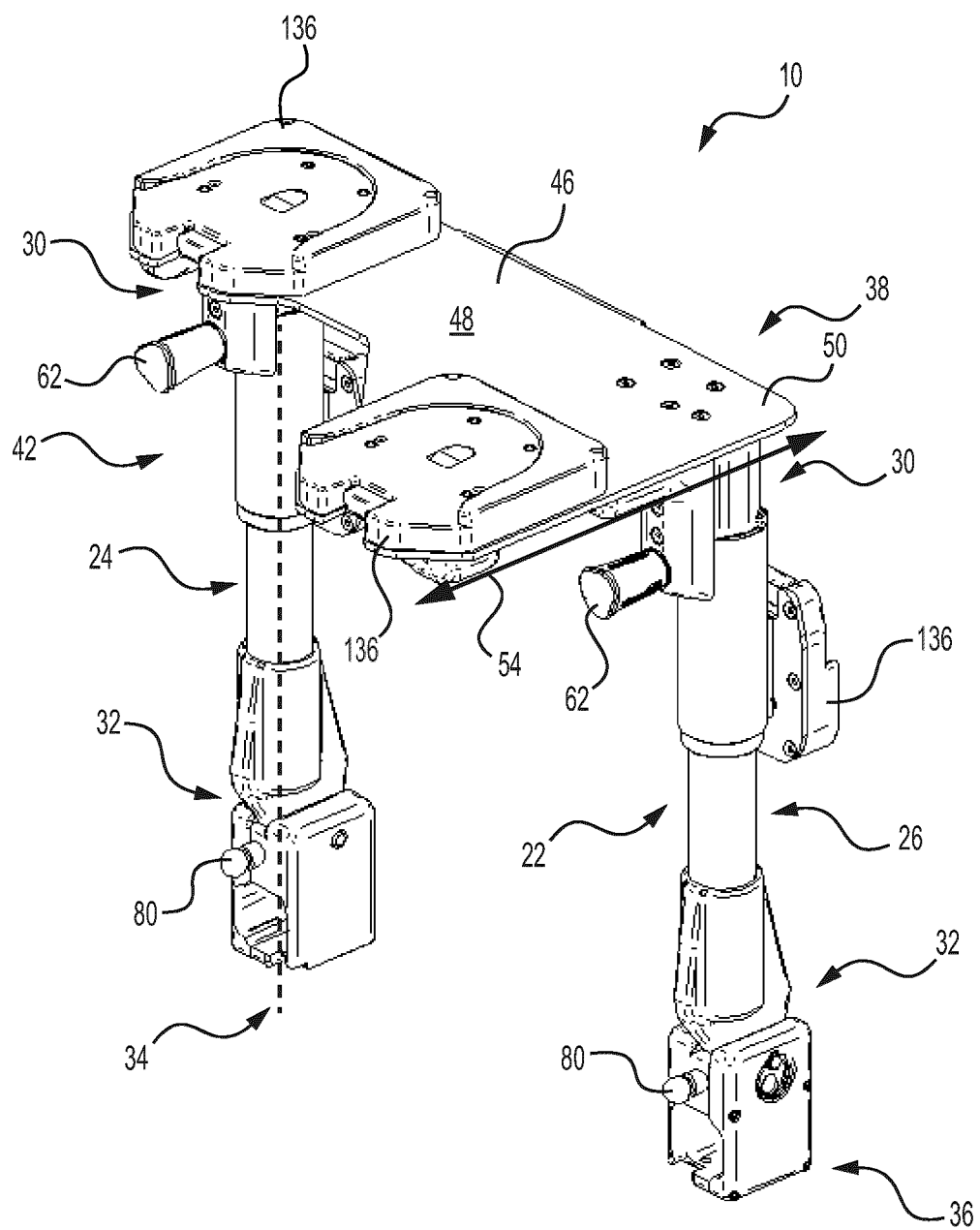
FIG. 1 is a perspective view from a first side of a mounting apparatus, according to certain embodiments of the present disclosure.

The present disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting. The use of "including", "comprising", or "having", "containing", "involving" and variations thereof herein, is meant to encompass the items listed thereafter as well as, optionally, additional items. In the following description, the same numerical references refer to similar elements.

Broadly, with reference to FIGS. 1-17, there is provided a mounting apparatus 10 for securing equipment 12 to a patient transport system 14. In certain embodiments, the mounting apparatus 10 is moveably attached to the patient transport system 14 and can be configured in different positions with respect to the patient transport system. The ability to place the mounting apparatus in different positions relative to the patient transport system 14 enables differing positions of the equipment 12 relative to the patient transport system 14. This can provide flexibility in terms of access to the patient in the patient transport system 14 as well as ease of manoeuvering the patient into and out of the patient transport system 14 by the ability of moving the equipment away during the transition. The mounting apparatus 10 is also arranged to be removed from and attached to the patient transport system without requiring any tools or specialized equipment.

As best seen in FIGS. 9-15, the equipment 12 is medical equipment, which may or may not be mobile. The equipment 12 can be any type of equipment that accompanies a patient during transit in the vehicle, such as ventilators, pumps, monitoring equipment, dialysis machines, drug delivery apparatus, screen, tablet, drips, etc. In other embodiments, the equipment 12 is other types of equipment which is required to be transported with the patient.

In the embodiments illustrated in FIGS. 5-17, the patient transport system 14 comprises a stretcher. The configuration of stretcher to which embodiments of the present technology can be applied is not limited. In other embodiments (not shown), the patient transport system 14 may comprise any other type of personal transport system arranged to transport the patient, such as a wheelchair or a bed. Embodiments of the mounting apparatus will be described and illustrated herein in relation to the stretcher but can be embodied for use with other patient transport systems 14. In this respect, the patient transport system 14 comprises any suitable transportation mechanism 16 for allowing transportation of the patient transport system 14, and a support body 18 for supporting the patient. The mounting apparatus 12 is arranged to be connected to at least a portion of the patient transport system 14. In the case of the stretcher of FIGS. 5-17, the transportation mechanism 16 comprises, at least in part, wheels. The support body 16 is a bed having a stretcher frame 20 to which the mounting apparatus 10 can be attached.

Referring now to FIGS. 1 to 8, in which there are shown certain embodiments of the mounting apparatus 12.

Broadly, the mounting apparatus 10 comprises a frame-like structure (frame 22) which can be pivotably attached to the patient transport system 14, and to which equipment 12 can be attached.

Figure 17A:
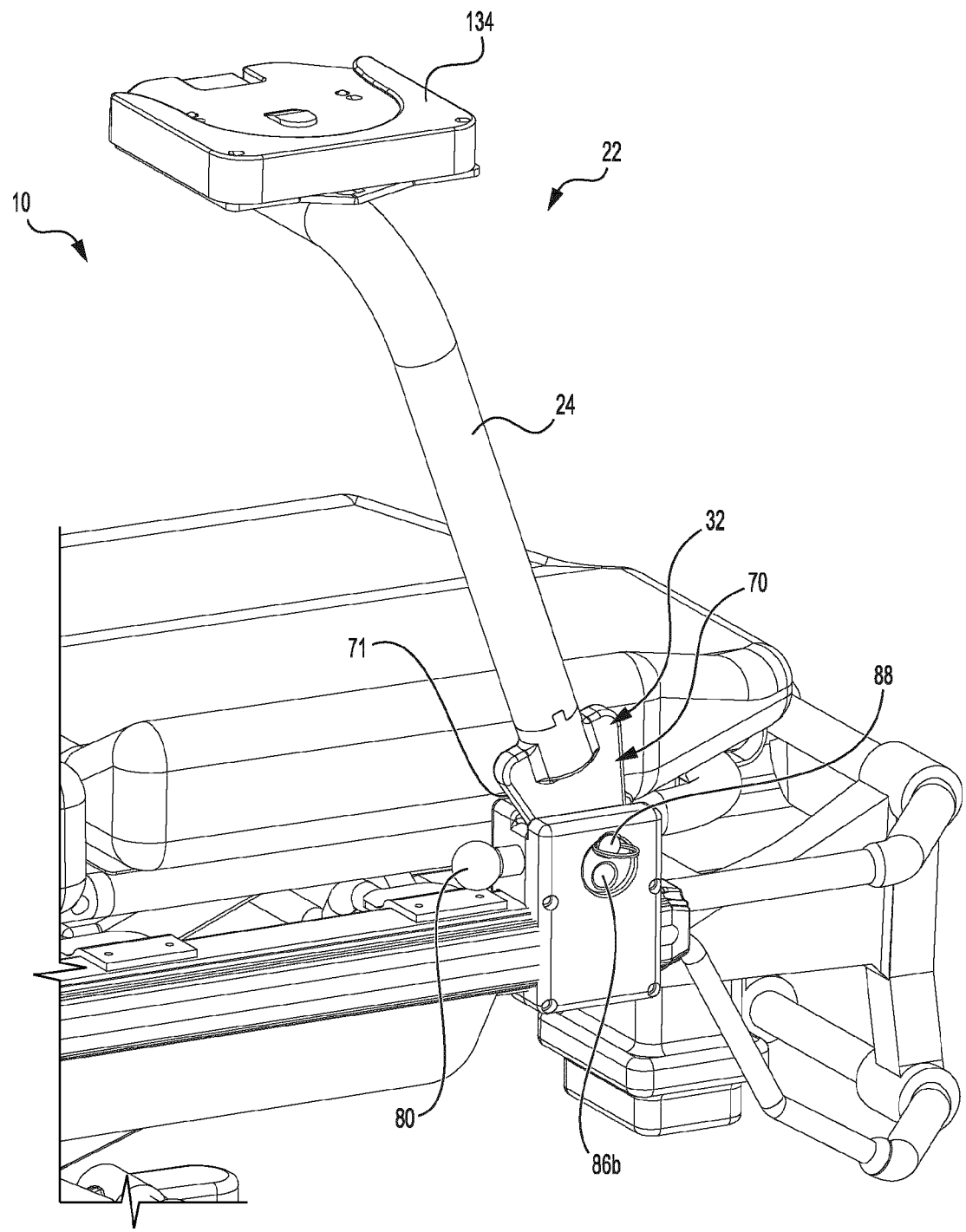
FIG. 17A is a side view of another embodiment of the mounting apparatus of FIG. 1 when attached to a patient transport system and in the upright position, according to certain embodiments of the present disclosure.
Figure 17B:
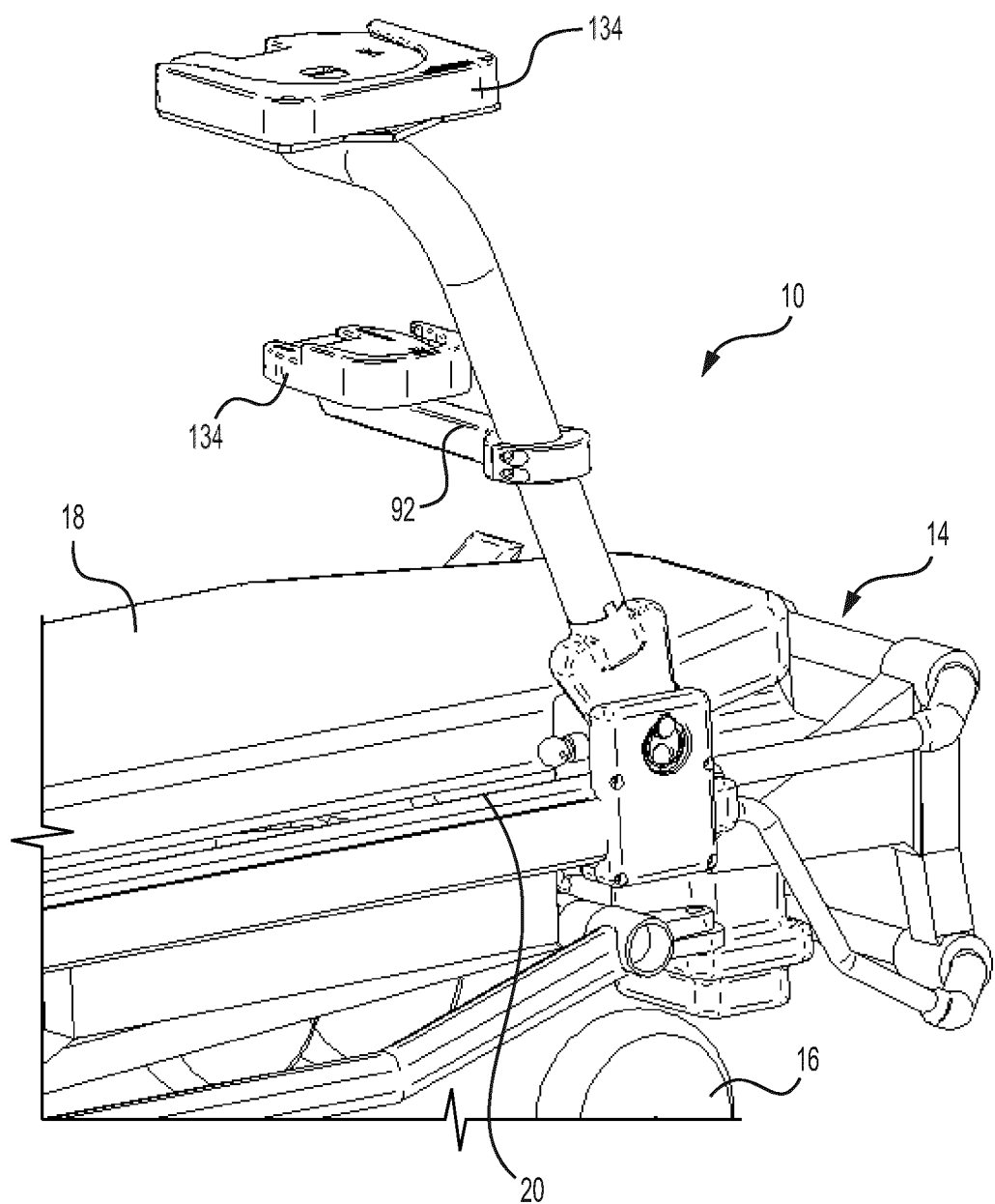
FIG. 17B is a side view of another embodiment of the mounting apparatus of FIG. 17A, according to certain embodiments of the present disclosure.

In certain embodiments, the frame 22 has substantially "U" shaped configuration (FIGS. 1-16). In certain other embodiments, the frame 22 has a substantially linear configuration (FIG. 17A and FIG. 17B). Other configurations of the mounting apparatus are also possible.

Turning first to the embodiments of FIGS. 1-16, the frame 22 comprises a first arm 24, a second arm 24 and a connecting member 26 connecting the first arm 24 and the second arm 26. Each of the first arm 24 and the second arm 26 has a distal end 30 and a proximal end 32. The first and second arms 24, 26 each have a longitudinal axis 34 which are substantially parallel to one another and spaced therefrom by the connecting member 28. It will be appreciated that the configuration of the frame of the mounting apparatus 10 may differ from that illustrated when the first arm 24 and the second arm 26 have different lengths.

Figure 8:
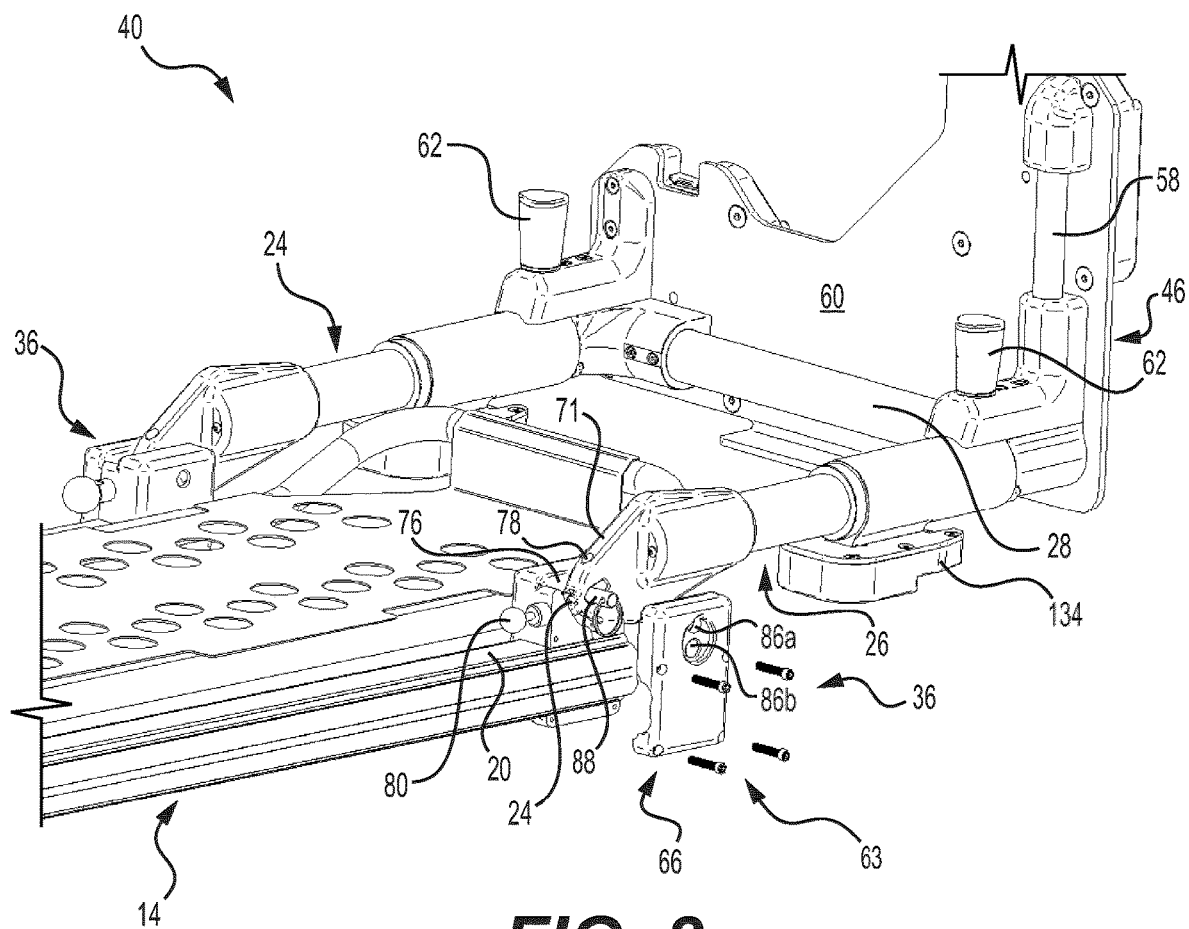
FIG. 8 is a perspective view from the first side of the mounting apparatus of FIG. 5 when attached to a patient transport system and in the reclined position, according to certain embodiments of the present disclosure.
Figure 9:
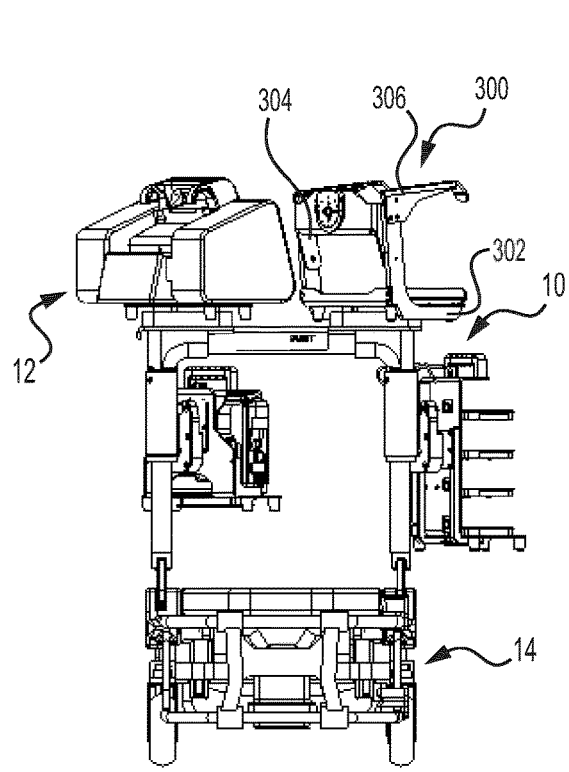
FIG. 9 is a view from the second side of the mounting apparatus of FIG. 1 with equipment attached thereto and when attached to a patient transport system and in the upright position, according to certain embodiments of the present disclosure.
Figure 10:
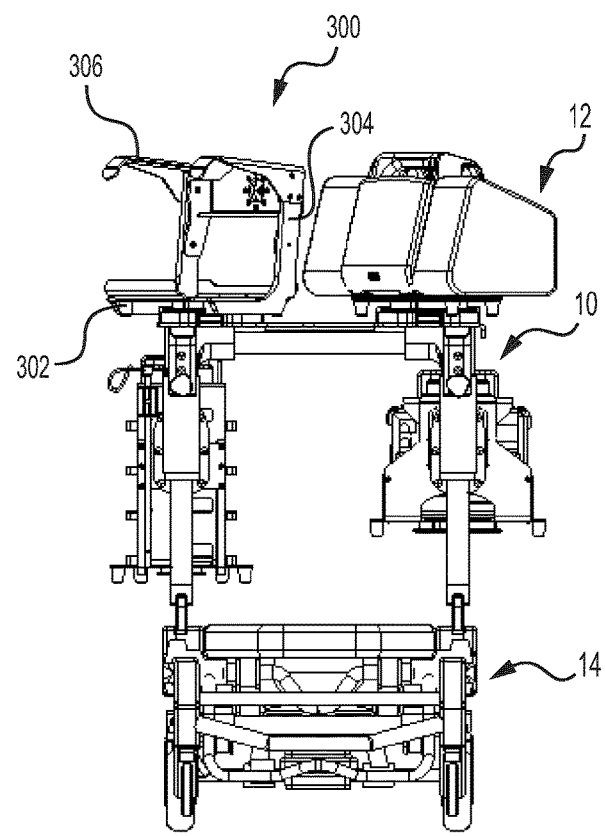
FIG. 10 is a view from the first side of the mounting apparatus of FIG. 9, according to certain embodiments of the present disclosure.
Figure 11:
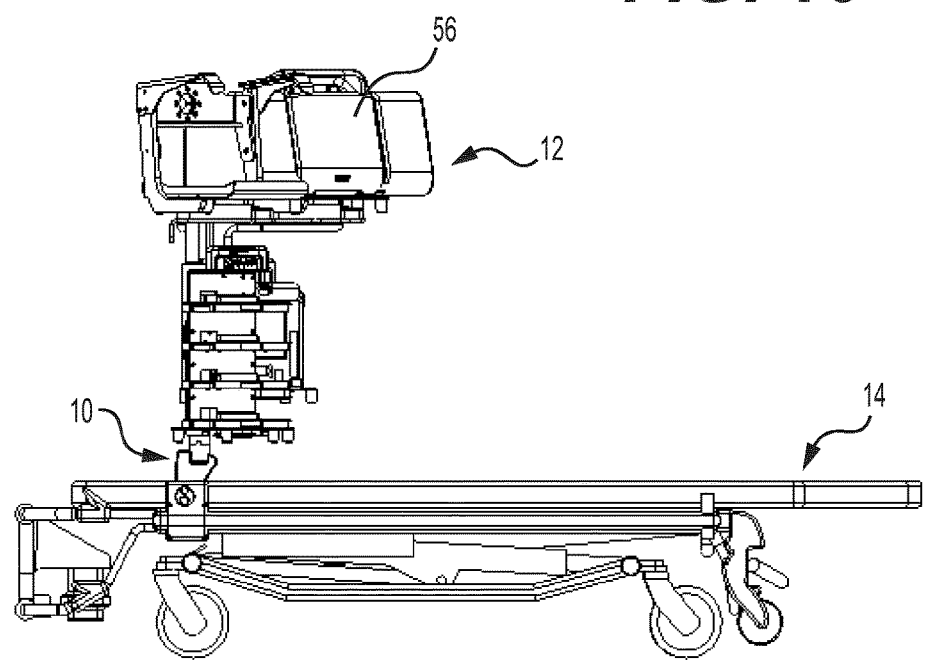
FIG. 11 is a plan view from another side of the mounting apparatus of FIG. 9, according to certain embodiments of the present disclosure.
Figure 12:
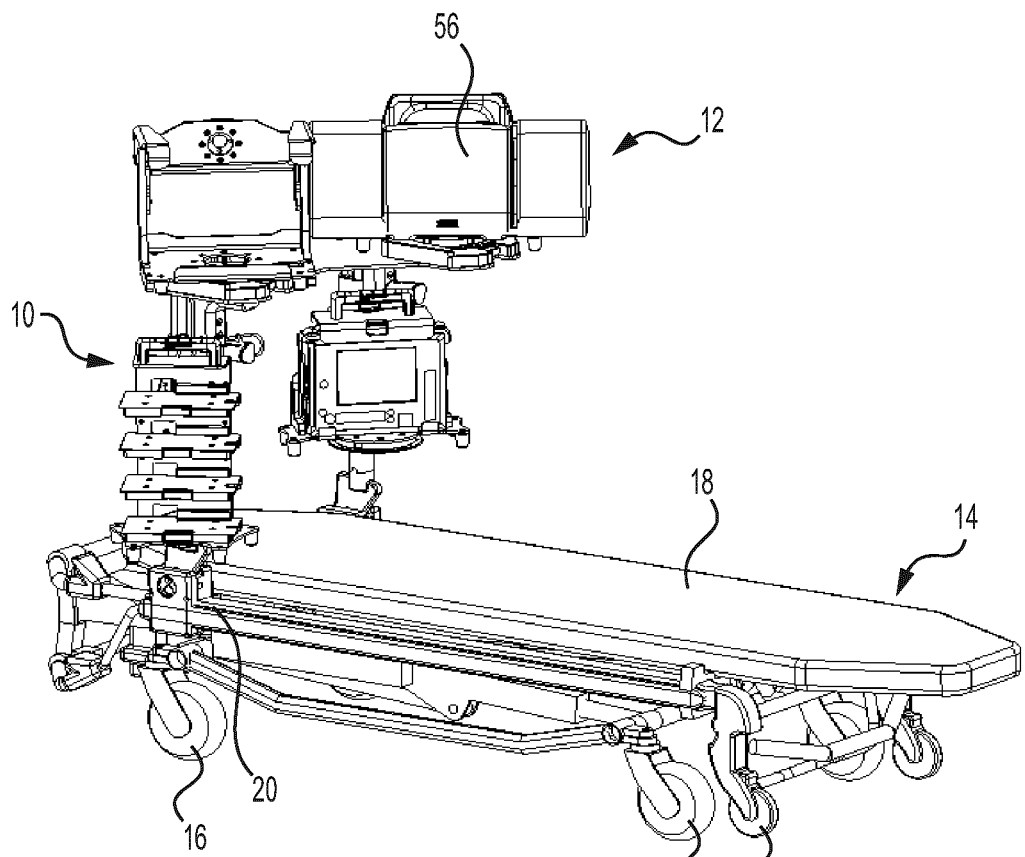
FIG. 12 is another perspective view from the first side of the mounting apparatus of FIG. 9, according to certain embodiments of the present disclosure.
Figure 13:
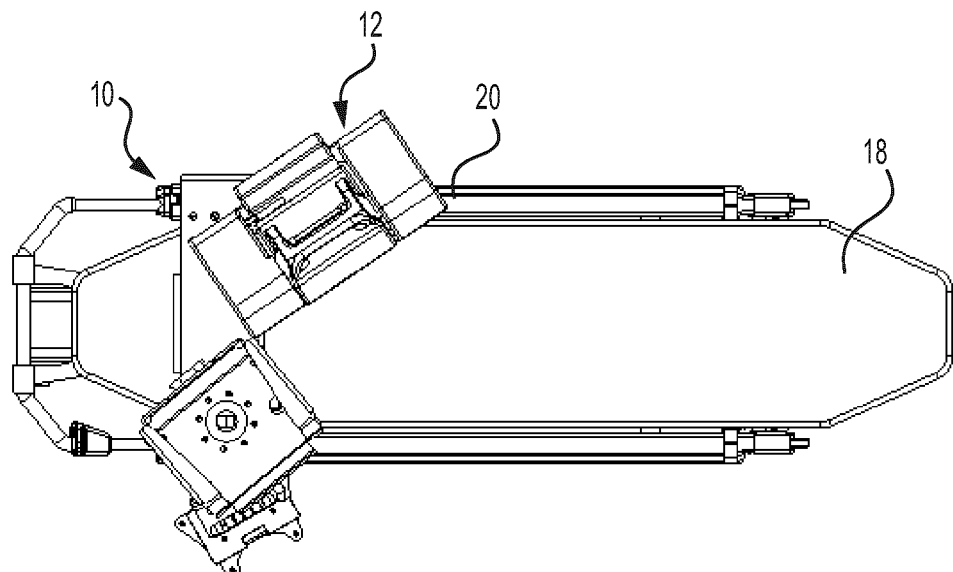
FIG. 13 is a top plan view of the mounting apparatus of FIG. 9, according to certain embodiments of the present disclosure.
Figure 14:
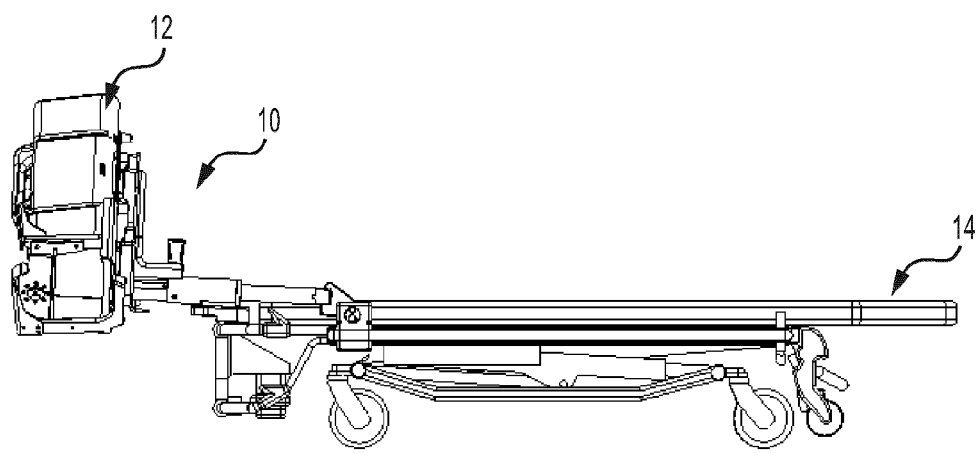
FIG. 14 is a plan view from yet another side of the mounting apparatus of FIG. 9, according to certain embodiments of the present disclosure.
Figure 15:
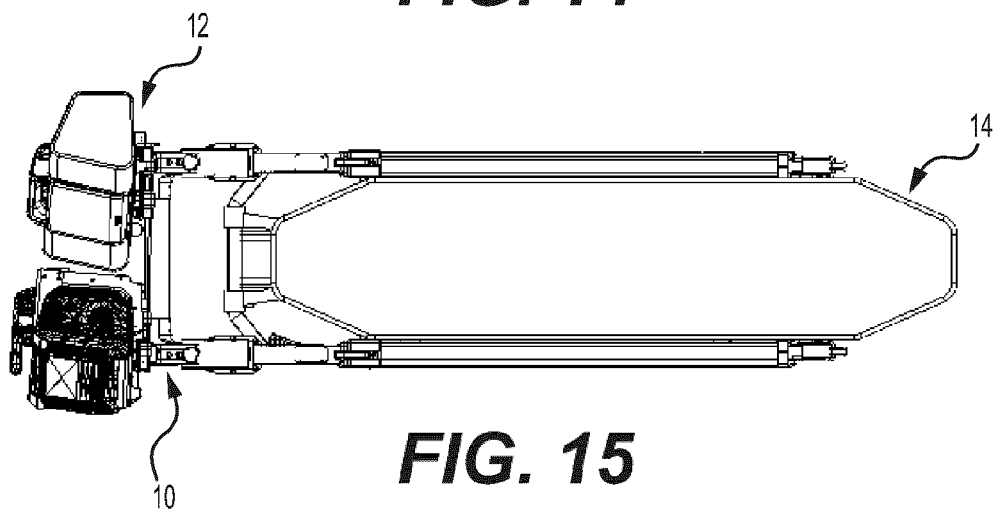
FIG. 15 is a bottom view from yet another side of the mounting apparatus of FIG. 9, according to certain embodiments of the present disclosure.
Figure 16:
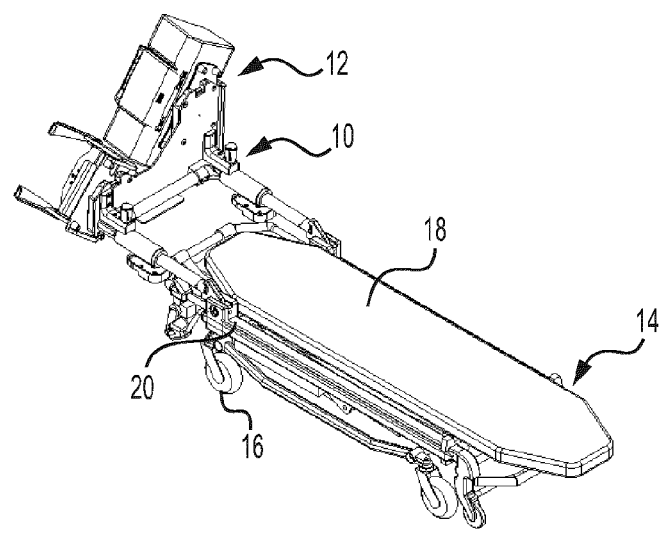
FIG. 16 is a perspective view from the first side of the mounting apparatus of FIG. 9, with equipment attached thereto, and in the reclined position, according to certain embodiments of the present disclosure.

The mounting apparatus 10 also has a clamping system 36 for removeably attaching the frame 22 to the patient transport system 14 and for allowing a rotation or pivoting of the frame 22 relative to the patient transport system 14 between an upright position 38 (FIG. 5) and a reclined position 40 (FIG. 8). In this respect, the clamping system 36 is provided at the respective proximal ends 32 of each of the first arm 24 and the second arm 26. The frame 22 has a first side 42 which faces the patient transport system 14 (and thereby also faces the patient when the patient is being supported by the patient transport system 14) when the frame 22 is in the upright position 38, and a second side 44 which faces away from the patient transport system 14 when the frame 22 is in the upright position 38. In the reclined position, the first side 42 faces upwardly and the second side 44 faces downwardly. The first side 42 can also be referred to as the patient-facing side.

Figure 2:
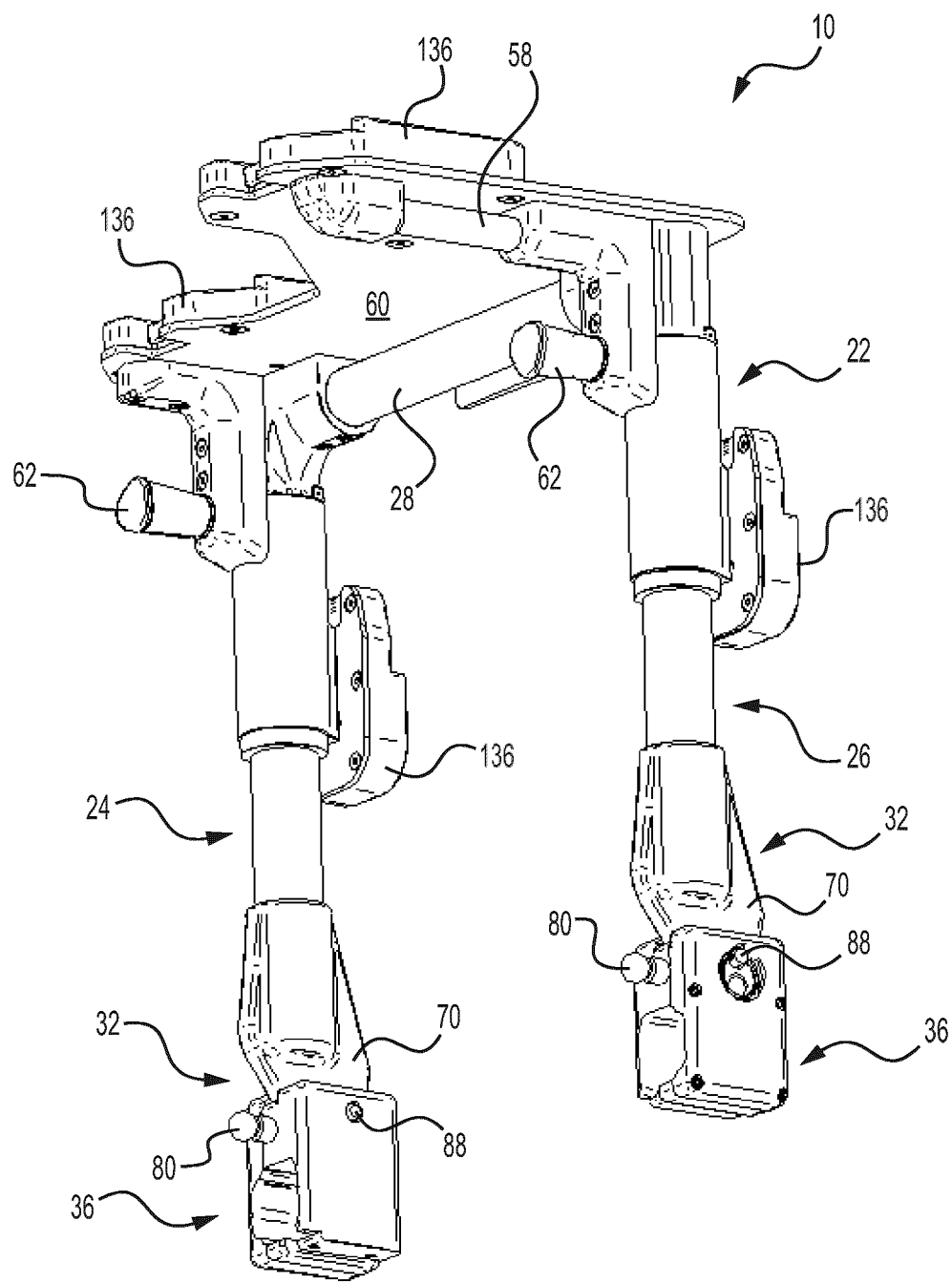
FIG. 2 is a perspective view from a second side of the mounting apparatus of FIG. 1 with a partially exploded view of a portion of a coupling device, according to certain embodiments of the present disclosure.
Figure 3:
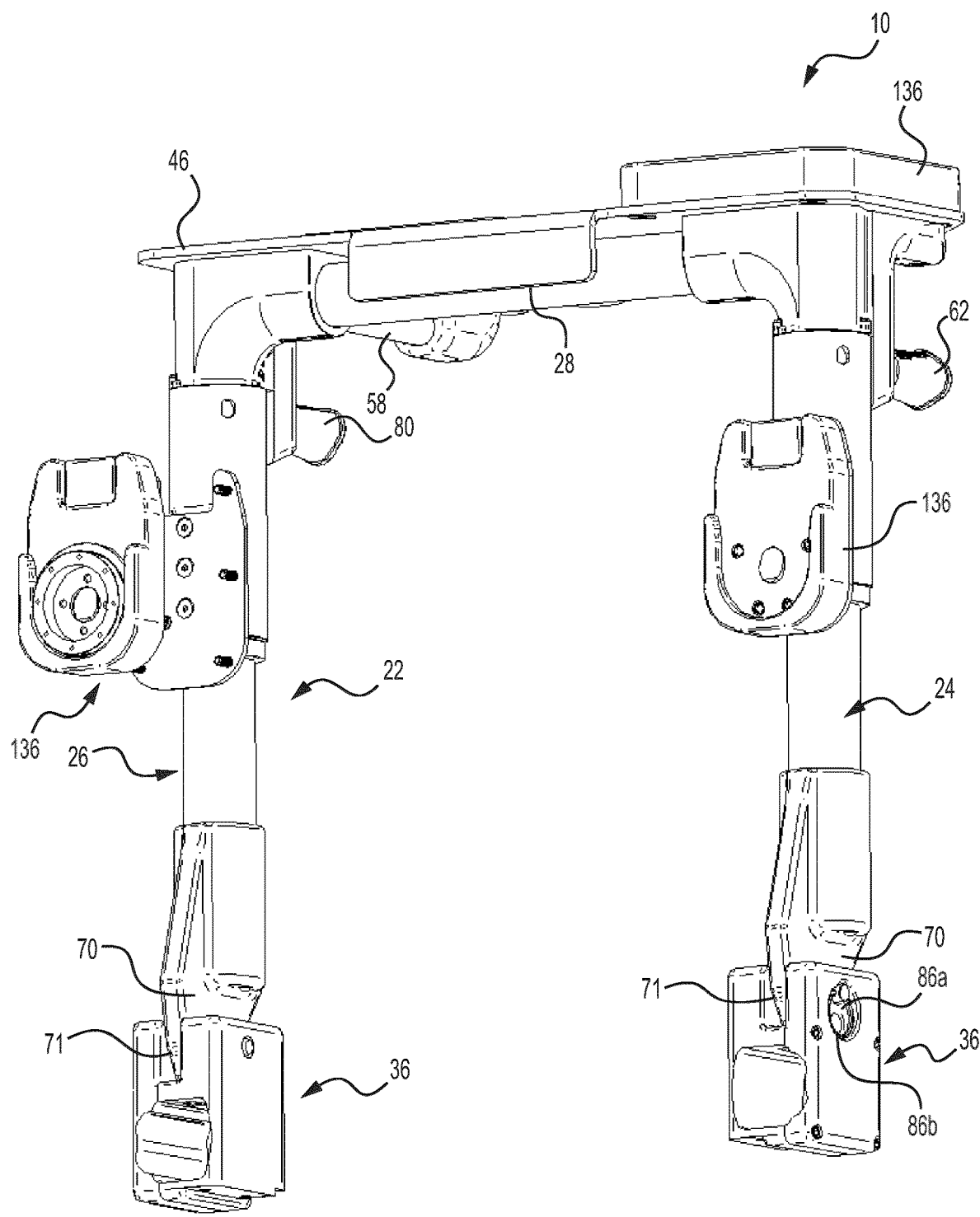
FIG. 3 is another perspective view from the second side of the mounting apparatus of FIG. 2, according to certain embodiments of the present disclosure.
Figure 4:
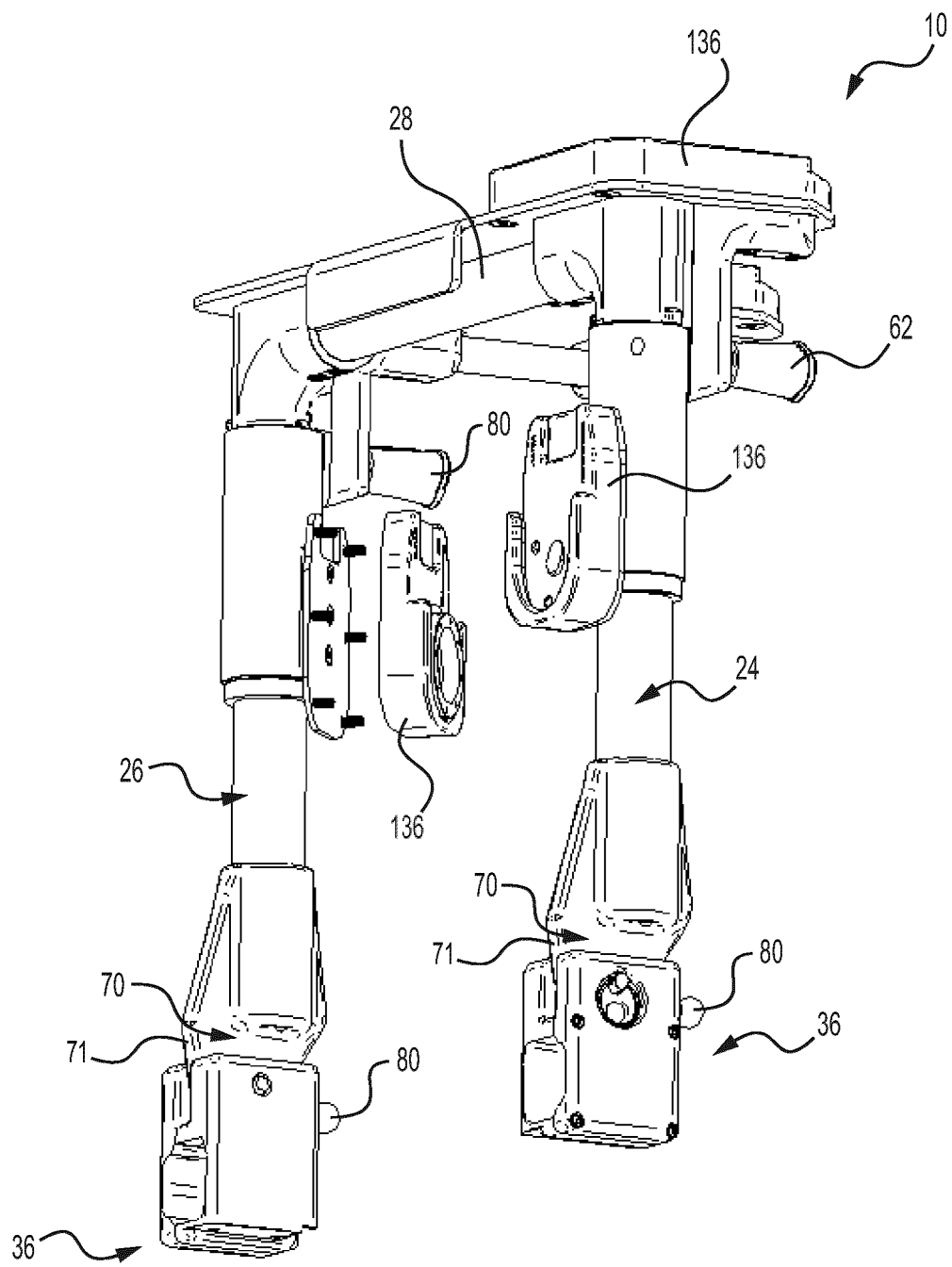
FIG. 4 is yet another perspective view from the second side of the mounting apparatus of FIG. 1, according to certain embodiments of the present disclosure.
Figure 5:
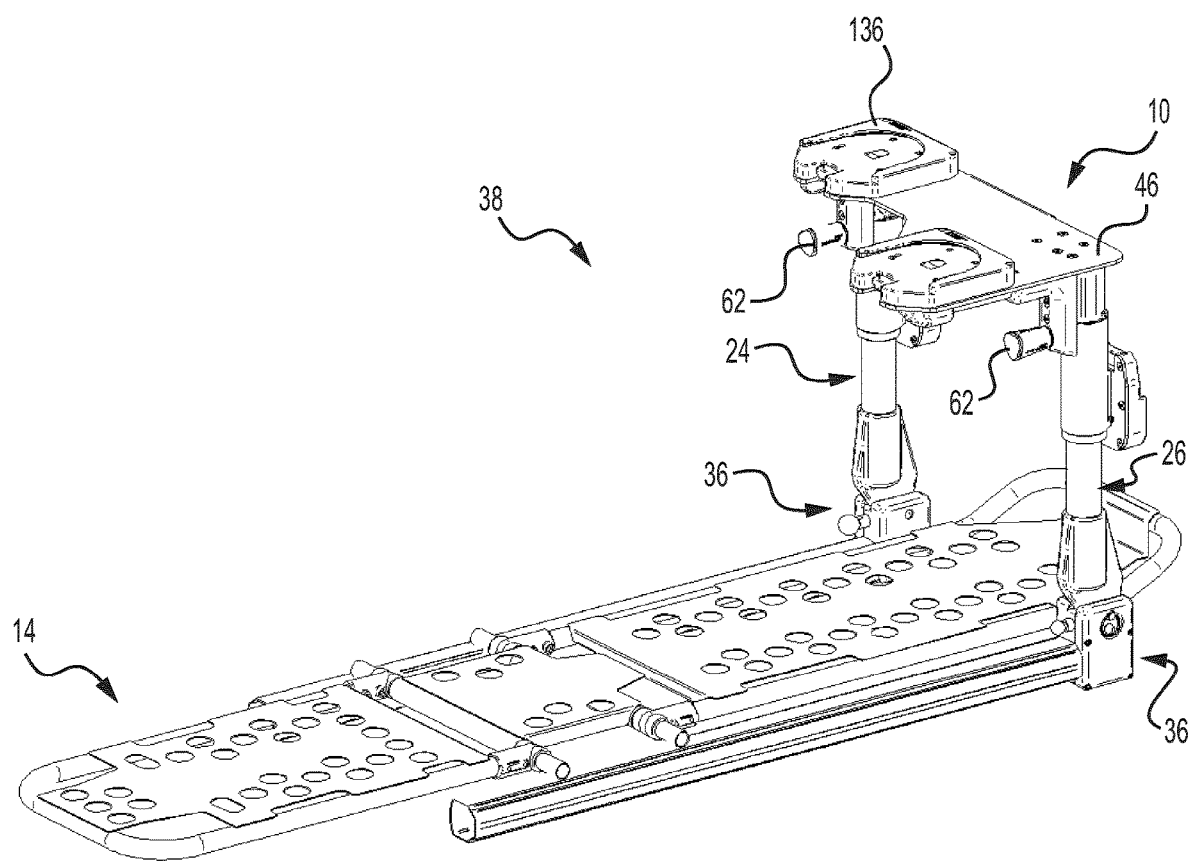
FIG. 5 is a perspective view from the first side of the mounting apparatus of FIG. 1 when attached to a patient transport system and in the upright position, according to certain embodiments of the present disclosure.

A platform 46 is provided at the distal ends 30 of the first arm 24 and the second arm 26, extending between the first and second arms 24, 26. The platform 46 is connected to one or more of the first arm 24, the second arm 26 and the connecting member 28. The platform 46 has a support face 48 with a support surface plane 50 which is substantially transverse to the longitudinal axes 34 of the first arm 24 and the second arm 26. The support face 48 has a flat construction. The support face 48 is sized and shaped to accommodate the equipment 12 to be attached to the frame 22. As best seen in FIGS. 1, 2 and 5, a width 54 of the platform 46 is variable between the first and second arms 24, 26. This can help to off-set a front face 56 (FIG. 9) of adjacent equipment 12 from one another for ease of use of personnel. Other configurations of the platform size and shape are possible and included within the scope of the present technology.

The mounting apparatus 10 is adapted to support equipment within a broad weight range. In this respect, in certain embodiments, the mounting apparatus 10 is provided with at least one transverse reinforcement member 58 extending along the platform 46, in a direction substantially transverse to the connecting member 28. The transverse reinforcement member 58 extends along an under face 60 of the platform 46. Other reinforcement members may be provided according to the load capacity of the mounting apparatus 10.

In the embodiments of FIGS. 1-8, at least one handle 62 is provided attached to the mounting apparatus 10 and arranged to provide a grip to a user during modulation of the mounting apparatus 10 between the upright position 38 and the reclined position 40. In certain embodiments, there are two handles 62, each handle extending from the first arm 24 and the second arm 26, and positioned proximally of the platform 46 and on the first side 42 of the frame 22. In other embodiments (not shown), the handles 62 may be provided on the second side 44 of the frame 22. In yet other embodiments, there may be less than, or more than, the two handles 62 illustrated herein.

Figure 6:
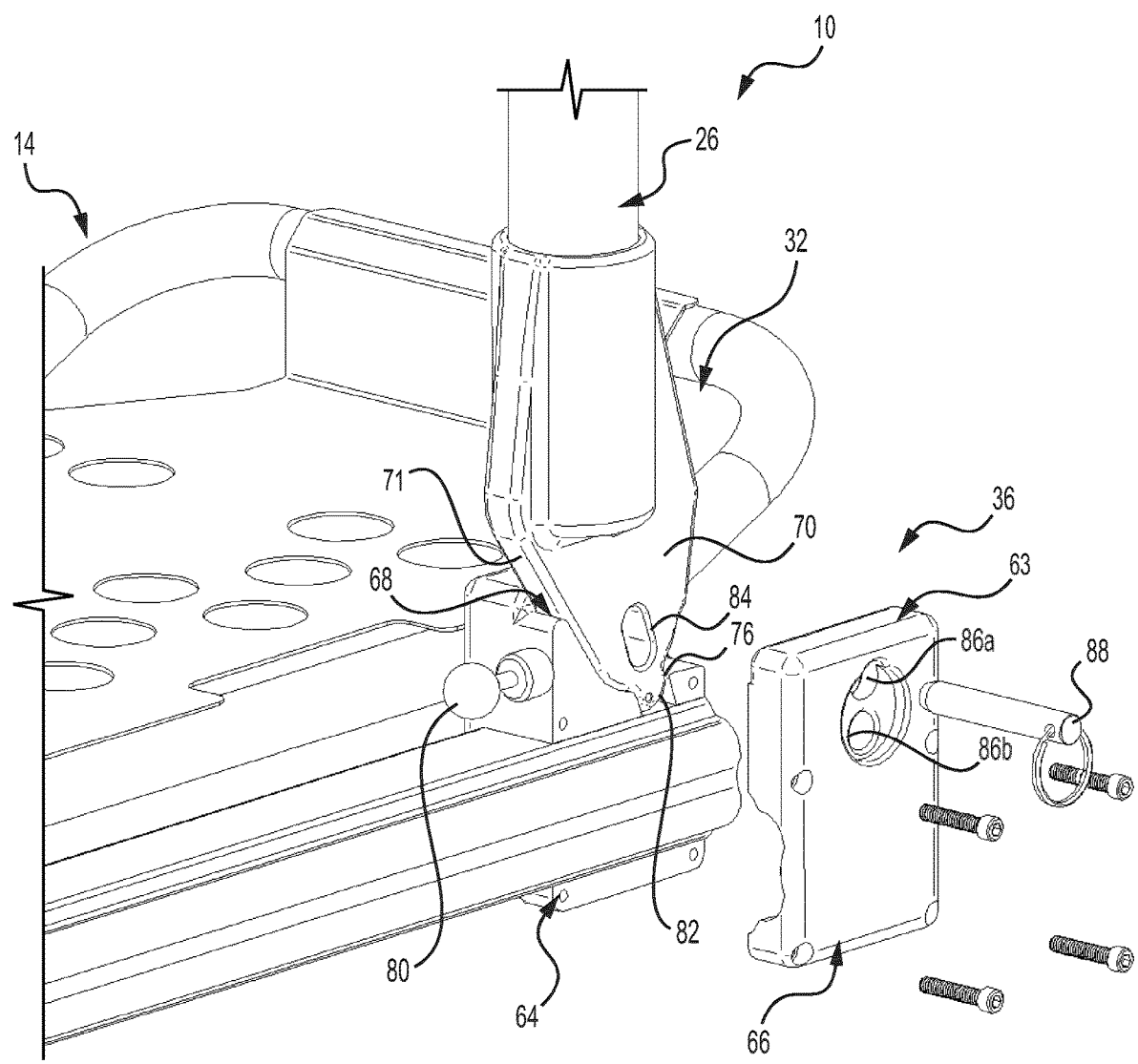
FIG. 6 is a close-up view of a clamping system of the mounting apparatus of FIG. 5, with the clamping system shown as a partially exploded, according to certain embodiments of the present disclosure.
Figure 7:
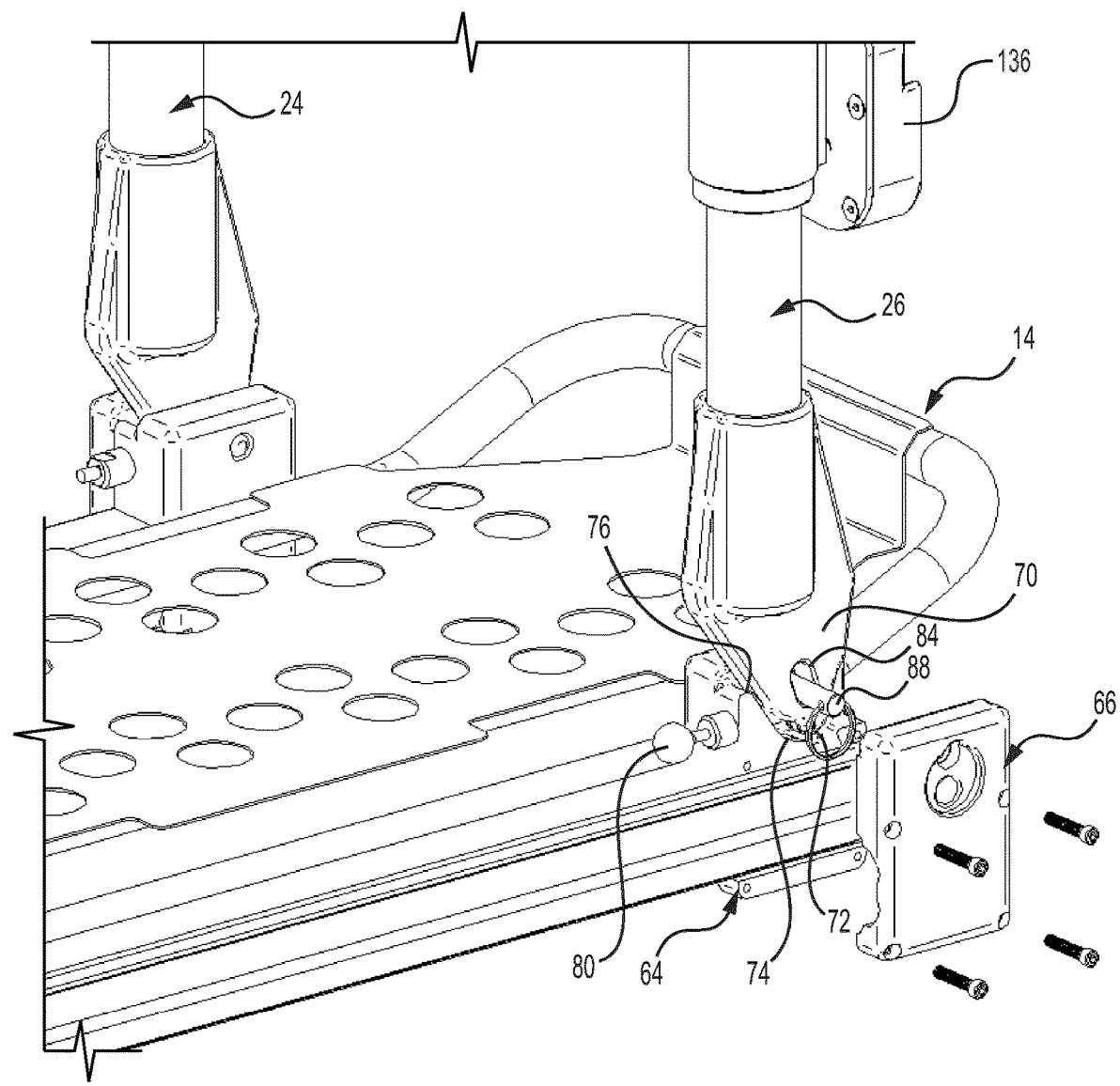
FIG. 7 is another close-up view of a clamping system of the mounting apparatus of FIG. 6, according to certain embodiments of the present disclosure.

Turning now to the clamping system 36, best seen in FIGS. 6-8. Each clamping system 36 comprises a body 63. In certain embodiments, the body 63 comprises a foot portion 64 and a cover portion 66. The foot portion 64 is configured to be attached to a part of the patient transport system 14, and the cover portion 66 arranged to be removeably attached to the foot portion 64 using fasteners, such as screws. In this respect, the foot portion 64 is recessed to receive a portion of the stretcher frame 20.

A slot 68 is defined in the body 63 for receiving the proximal end 32 of the respective first or second arm 24, 26. When assembled, the respective first or second arm 24, 26 extends upwardly from the body 63. In certain embodiments, assembly of the cover portion 66 and the foot portion 64 defines the slot 68. The slot 68 and the proximal end 32 of the respective arm 24, 26 have complementary form, such that the respective arm 24, 26 can be rotated or pivoted within the slot 68, along a plane parallel to the longitudinal axis 34 of the respective arm 24, 26 and transverse to the connecting member 28, between the upright position 38 and the reclined position 40.

The proximal end 32 of the respective arm 24, 26 comprises a flat end 70 with two parallel faces receivable in the slot 68. A profile of the flat end 70 is tapered, with a diameter of the first end 24 decreasing towards a tip at the proximal end. The flat end 70 has a rim (perimeter) 71 with teeth 72 which teeth are receivable within notches 74 defined in a wall 76 of the slot 68. A profile of the wall 76 is complementary to a profile of the rim 71. The rim 71 of the flat end 70 has a first opening 78 formed therein and engageable with a pin 80 extending through the body 63, such as the foot portion 64. The first opening 78 and the pin 80 are positioned relative to each other such that the pin is received in the first opening 78 when the frame 22 is in the upright position 38. This also helps to lock the upright position 38. The pin 80 is resiliently biased, such as using one or more springs, towards the opening 78.

The rim 71 of the flat end 70 has a second opening 82 formed therein and spaced from the first opening 78. The second opening 82 is also engageable with the pin 80. The second opening 82 and the pin 80 are positioned relative to each other such that the pin 80 is received in the second opening 82 when the frame 22 is in the reclined position 40. This also helps to lock the reclined position 40.

An elongate opening is defined in the flat end 70 of the respective arm 24, 26. Two cover portion openings 86 (an upper cover portion opening 86a and a lower cover portion opening 86b) are defined in the cover portion 66. When the foot portion 64 and the cover portion 66 are assembled, a position of the elongate opening 84 corresponds to a position of the cover portion openings 86. In other words, the cover portion openings 86 are overlaid over the elongate opening 84 when the foot portion 64 and the cover portion 66 are assembled.

The clamping system 36 further comprises a pivot pin 88 receivable in either one of the cover portion openings 86 and the elongate opening 84.

In the upright position 38, the pin 88 is received in the upper cover portion opening 86a, and the pin 80 is received in the first opening 78 of the rim 71, thereby retaining the frame 22 in the upright position 38.

To modulate the frame 22 to the reclined position, the resiliently biased pin 80 is pulled outwardly away from the clamping system 36 which causes the pin 80 to be disengaged from the first opening 78 of the rim 71 allowing rotation or pivoting of the frame 22 to the reclined position. A bearing 90 is provided to prevent or reduce wear and facilitate rotation or pivoting of the respective arm 24, 26 in the slot of the clamping system. Once in the reclined position 40, this position can be retained by moving the pivot pin 88 to the lower cover portion opening 86b and by engaging the pin 80 with the second opening 82 in the rim 71.

Turning now to FIGS. 17A and 17B in which are shown embodiments of the mounting apparatus 10 in which the frame comprises a linear configuration instead of the "U" configuration. More specifically, the embodiments of FIGS. 17A and 17B, differ from that of FIGS. 1-16 in that the mounting apparatus 10 comprises a single arm, such as the first arm 24 or the second arm 26, together with the clamping system 36.

Referring to FIG. 17A, the frame 22 of the mounting apparatus 10 comprises a single arm, such as the first arm 24 having the distal end 30, the proximal end 32 and the longitudinal axis 34. In this embodiment, there is no second arm 26, no connecting member 28, and no platform 46. The mounting apparatus 10 of FIG. 17A includes the clamping system 36 which is configured to pivotably attach the frame 22 to the patient transport system 14 and to selectively retain the frame 22 in one or both of the upright and reclined positions.

The clamping system 36 of FIG. 17A is the same as that described and illustrated in FIGS. 1-16. Broadly, the clamping system 36 comprises the slot 68, which is sized and shaped to receive the flat end 70 at the proximal end 32 of the first arm 24 and to permit the first arm 24 to pivot about the pivot pin 88 along the plane parallel to the longitudinal axis 34 between the upright and reclined positions. Interengaging elements are provided between the proximal end of the first arm 24 and the wall 76 of the slot which help to guide the pivoting movement of the first arm 24. In certain embodiments, the interengaging elements comprise teeth 72 protruding from the rim 71 at the proximal end of the first arm 24, which are engageable with the notches 74 defined in the wall 76 of the slot 68. In other embodiments, the teeth may be provided in the wall 76 and the notches in the rim 71.

In the upright position 38, movement of the frame 22 in a first direction (e.g. towards the stretcher bed) is delimited by abutment of a portion of the rim 71 against the wall 76. Movement of the frame 22 in a second direction (e.g. towards the reclined position) is delimited by abutment of another portion of the rim 71 against the wall 76.

Locking of the frame 22 in the upright position is by virtue of engagement of the pin 80 with the first opening 78 (FIG. 8). Locking of the frame 22 in the reclined position is by virtue of engagement of the pin 80 with the second opening 82. The frame 22 is modulated from the upright position to the reclined position, by pulling the resiliently biased pin 80 outwardly causing the pin 80 to be disengaged from the first opening 78 in the rim 71. The frame 22 can then be pivoted to the reclined position. Releasing the pin 80, enables its engagement with the second opening 82 in the rim 71 to lock the reclined position.

The frame 22 is removable from the clamping system by removing the pivot pin 88 from the elongate slot 84.

Referring to FIG. 17B, the mounting apparatus differs from that of FIG. 17A in that it includes an extension arm 92 extending from the first arm 24.

In certain embodiments of any of FIGS. 1-17B, one or more coupling devices 100 are provided for releasably attaching the equipment 12 to the frame 22. The one or more coupling devices may be attached to the frame 22. Certain embodiments of such coupling devices 100 will now be described in relation to FIGS. 18-28.

The coupling device 100 comprises a base member 134 connectable to a portion of the frame 22 of the mounting apparatus 10, and a release member 136 connectable to the equipment 12, the base member 134 and the release member 136 being releasably connectable together in a coupled position.

The release member 136 has a body 138 which is plate-like and has a first side 140 and a second side 142. The first side 140 of the release member body 138 defines a planar contact face 144 for contacting the base member 134. The second side 142 of the release member 136 has a collar 146 extending therefrom, the collar 146 positioned inwardly of a perimeter 148 of the release member 136 to define a flange portion 150 of the release member 136.

The base member 134 has a front side 152 and a back side 154. The front side 152 has a planar contact portion 156 for contacting the contact face 144 of the release member 136. A shoulder 158 extends around a portion of a periphery 160 of the planar contact portion 156 to define a pocket 162 for receiving at least a portion of the release member 136. The shoulder 158 is engageable with a portion of the flange 150 of the release member 36 when the release member 136 is positioned on the base member 134.

The base member front side 152 has an open access end 164 through which the release member 136 can be slidingly inserted and removed from the pocket 162. As can be seen, the base member 134 is four-sided, with the shoulder 158 extending around three of the four sides and the fourth side being the open access end 164. In other embodiments, the base member 134 may have different numbers of sides.

Figure 18:
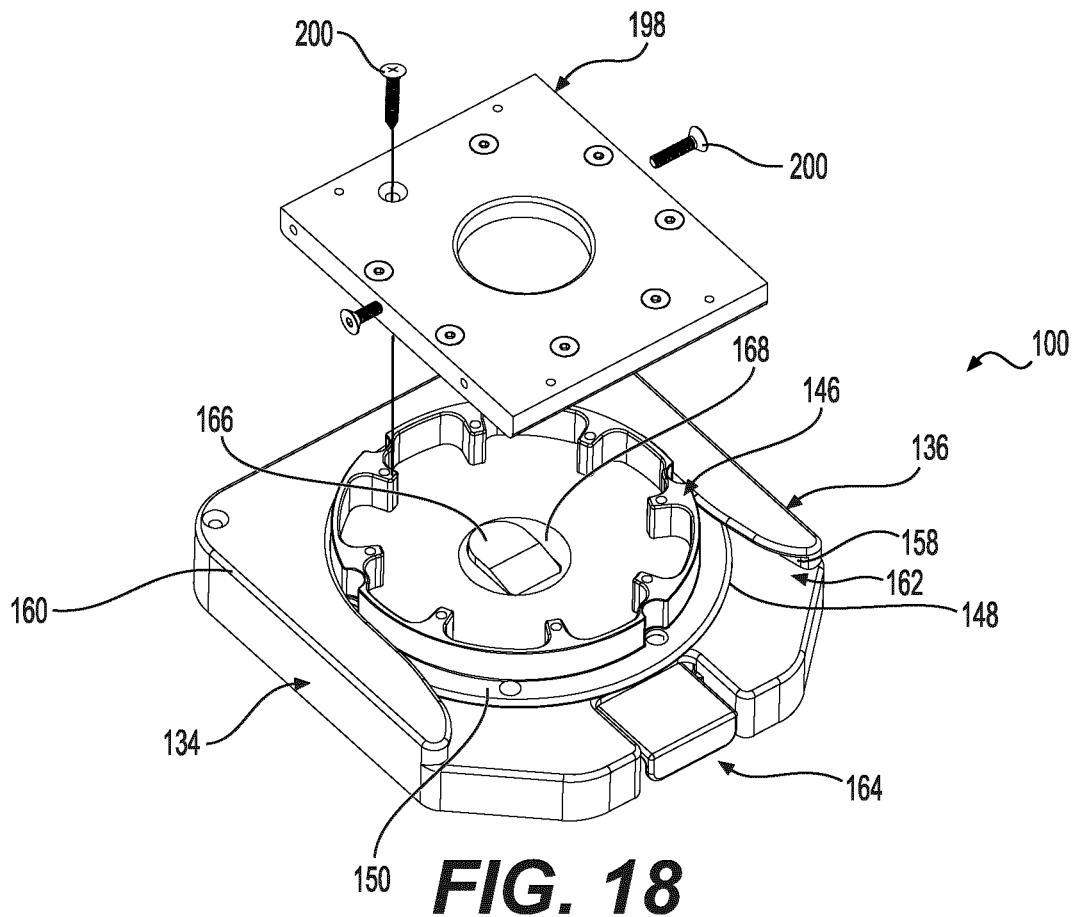
FIG. 18 is a coupling device comprising a base member, a release member, and a top plate, according to certain embodiments of the present disclosure.
Figure 19:
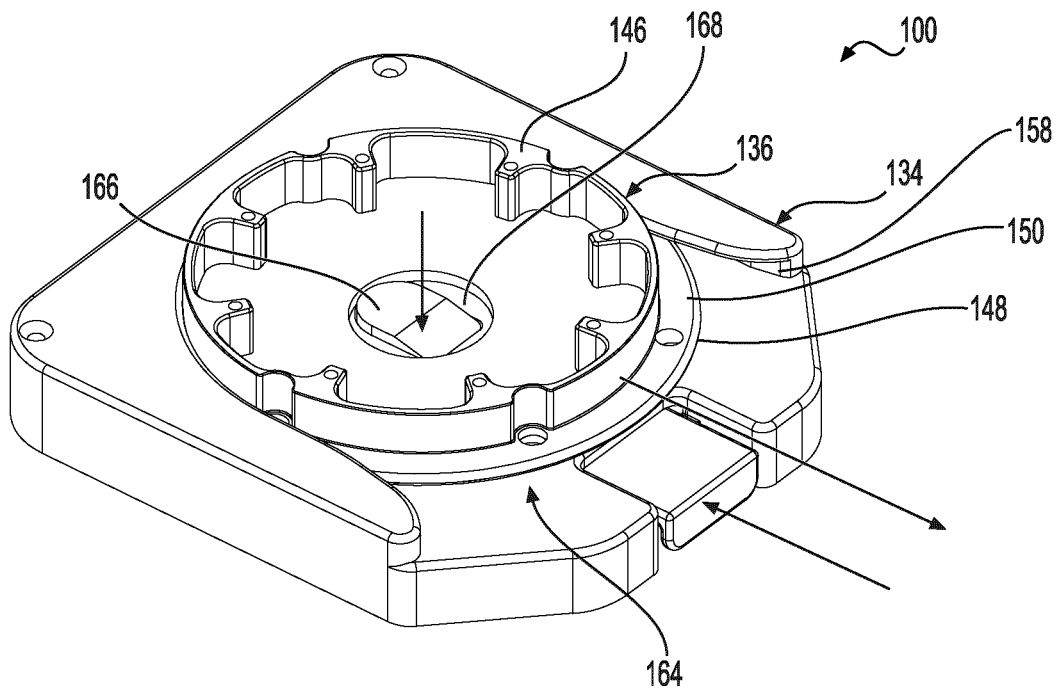
FIG. 19 is the coupling device of FIG. 18, with the top plate removed for clarity, when in the coupled and lock position, according to certain other embodiments of the present disclosure.
Figure 20:
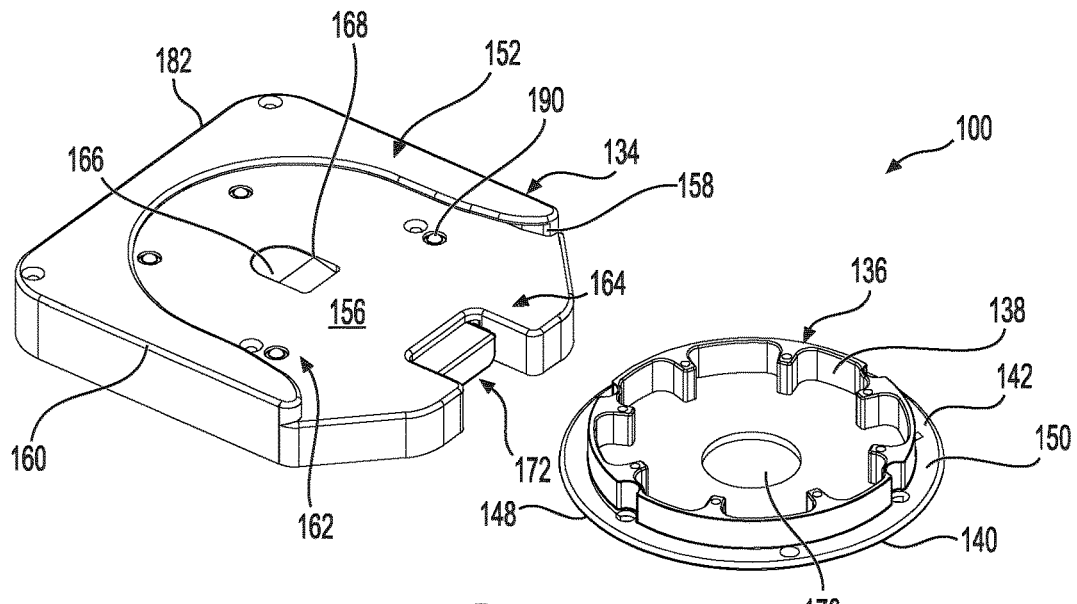
FIG. 20 is the coupling device of FIG. 18, when in the uncoupled and unlock position, according to certain other embodiments of the present disclosure.
Figure 21:
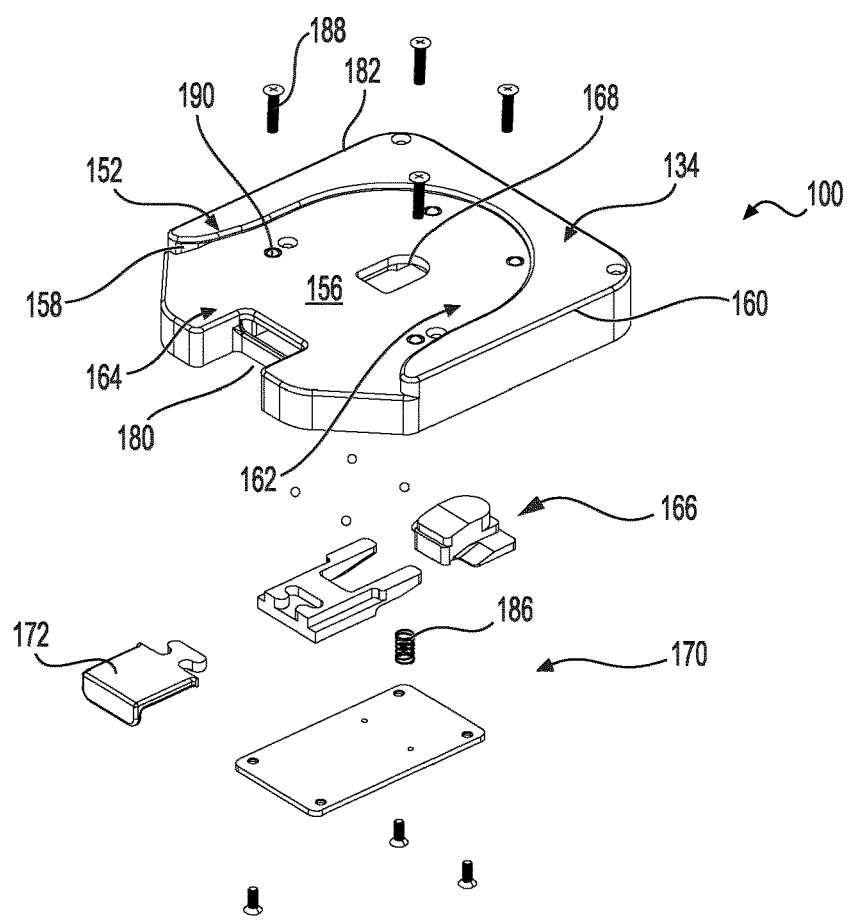
FIG. 21 is an exploded view of the base member of FIG. 18, according to certain other embodiments of the present disclosure.
Figure 22:
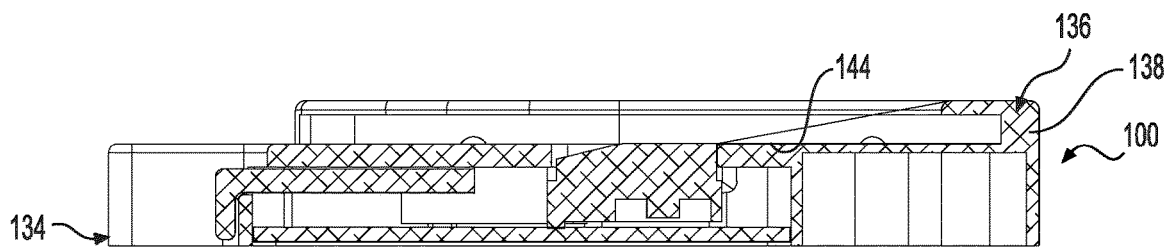
FIG. 22 is a cross-sectional view of the coupling device of FIG. 18, according to certain other embodiments of the present disclosure.

A stop member 166 is positioned in a recess 168 within the planar contact portion 156 of the base member 134 and is moveable relative to the planar contact portion 156. The stop member 166 is moveable to extend out of the recess 168 and to be housed fully in the recess 168 by a coupling lock mechanism 170 and an actuator 172. The stop member 166 is actuatable between a lock position in which at least a portion of the stop member 166 extends from the recess 168 and a release position in which the stop member 166 is retracted into the recess 168 and does not extend from the recess 168. In the lock position, when the base member 134 and the release member 136 are coupled together, the stop member 166 can abut an edge 174 of an opening 176 defined in the release member contact face 144 to delimit movement of the release member 36 towards the open access end 64 (FIGS. 18-20). In the release position, the release member 136 can be decoupled from the base member 134 (FIG. 20).

The actuator 172 is positioned at the open access end 164. In the embodiments illustrated in FIGS. 18 to 28, the actuator 172 is a push button 178 housed within a groove 180 formed at the open access end 164. The actuator 172 can be moved between a neutral position and a deployed position. When the actuator 172 is in the neutral position (FIG. 19), the stop member 166 is resiliently biased towards the lock position. As best seen in FIG. 20, when the actuator 172 is in the deployed position (pushed inwardly), the coupling lock mechanism 170 is arranged to move the stop member 166 to retract into the recess 168 in the release position. This can allow the release member 136 to be slid relative to the base member 134 and removed from the base member 134. In certain embodiments, the actuator 172 extends beyond a perimeter 182 of the base member 34 (FIG. 27) when in the neutral position. In other embodiments, the actuator 172 does not extend beyond the perimeter 182 of the base member 134 (FIGS. 18 to 26).

Figure 24:
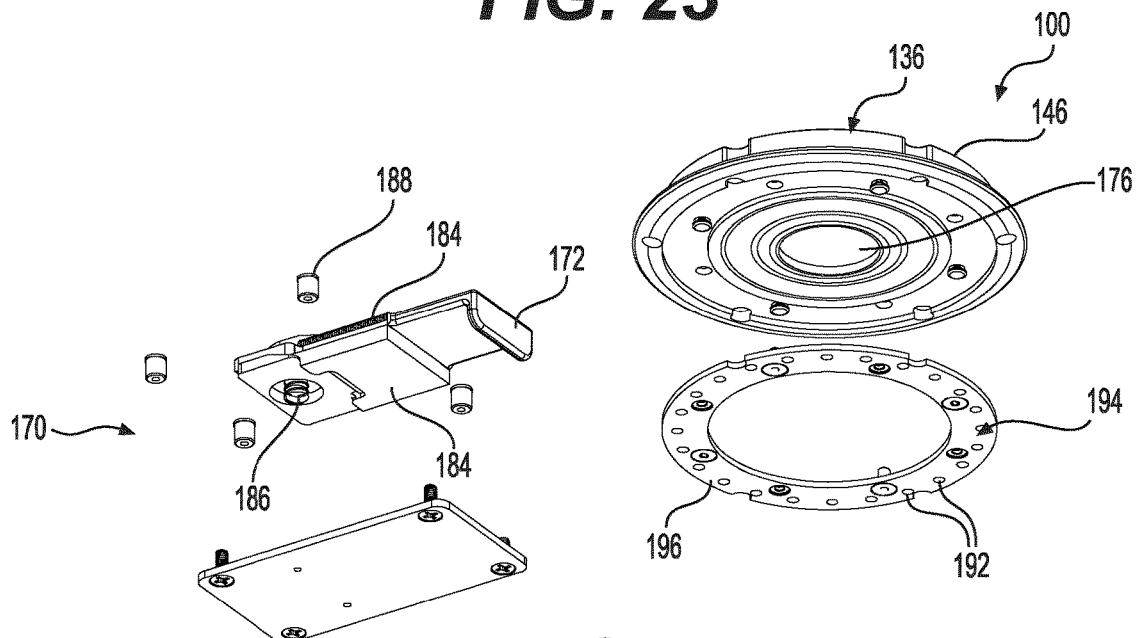
FIG. 24 is an exploded view of the release member of FIG. 18 and a lock mechanism, according to certain other embodiments of the present disclosure.
Figure 25:
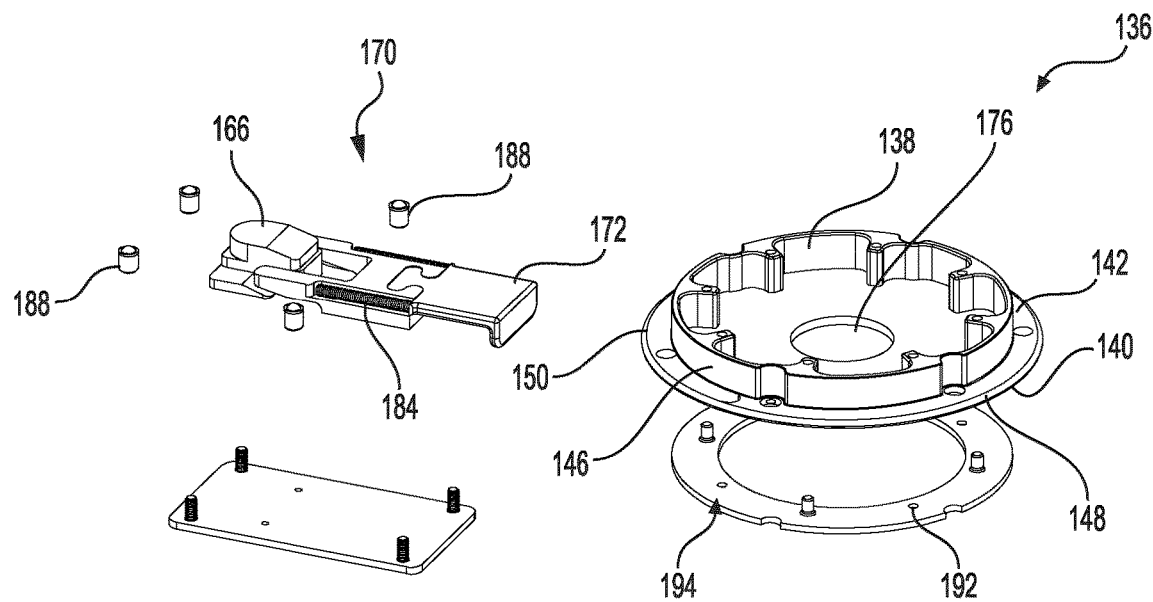
FIG. 25 is an exploded view of the release member of FIG. 18 and a lock mechanism, according to certain other embodiments of the present disclosure.
Figure 26:
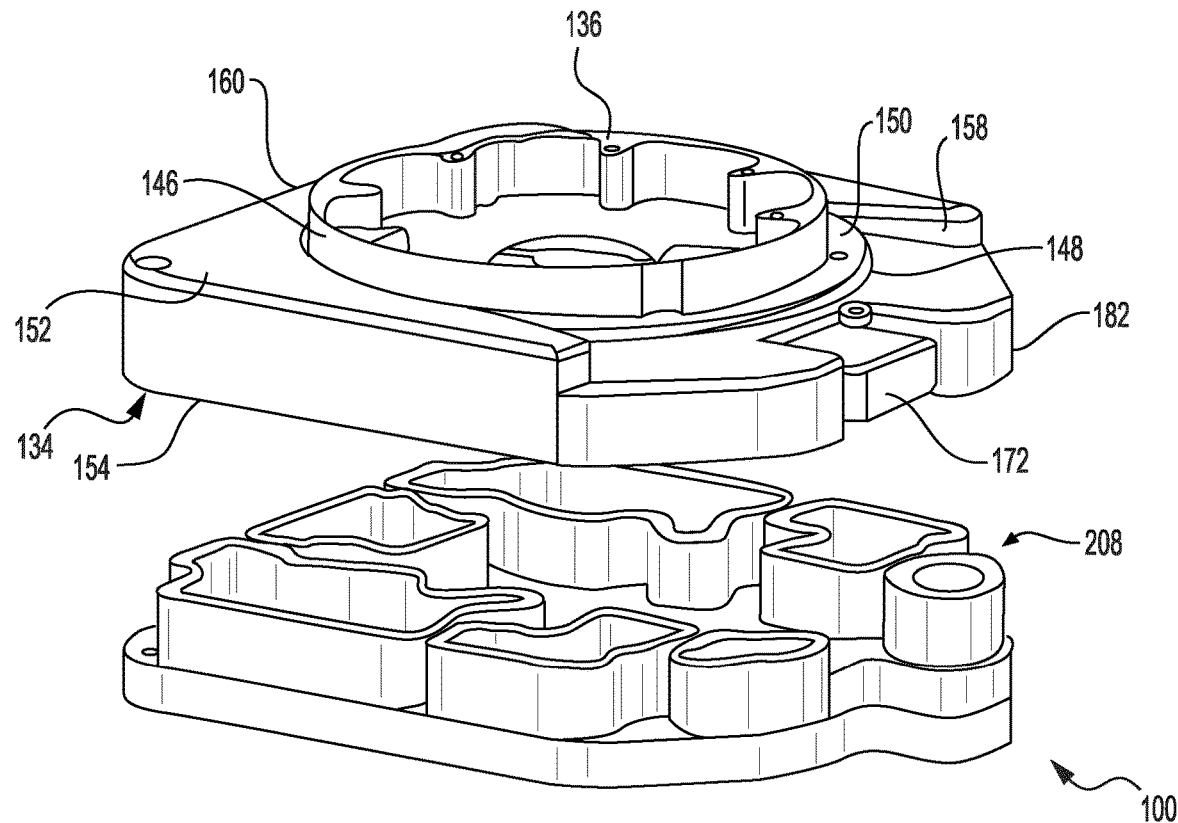
FIG. 26 is the base member of FIG. 18 and a damping member, according to certain other embodiments of the present disclosure.

The coupling lock mechanism 70, best seen in FIGS. 24 and 25, comprises an actuator spring 184 resiliently biasing the actuator 172 outwardly to the neutral position, and a stop member spring 186 resiliently biasing the stop member 166 to the lock position. The actuator spring 184 and the stop member spring 186 extend in directions which are substantially transverse to one another.

The base member 134 comprises a plurality of spring loaded ball bearings 188 partially extending from recesses 190 formed in the planar contact portion 156 of the front side 152 of the base member 134 and engageable with corresponding recesses 192 defined in the planar contact face 144 of the release member 136. The spring loaded ball bearings 188 and the recesses 192 can guide the movement of the release member 136 relative to the base member 134.

Figure 23:
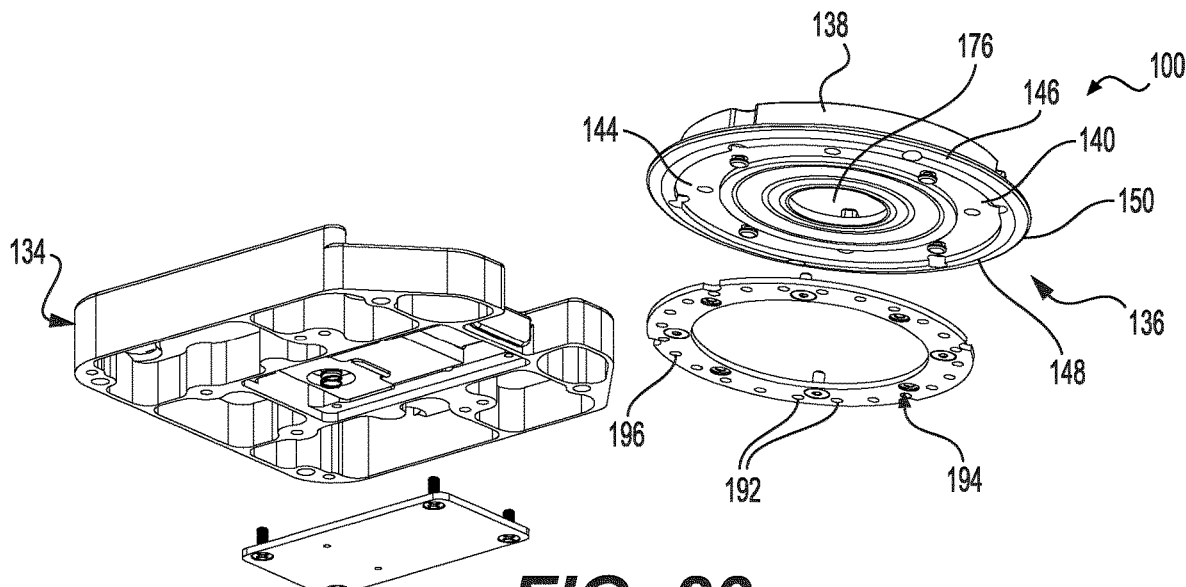
FIG. 23 is an exploded view of the base member and the release member of FIG. 18, according to certain other embodiments of the present disclosure.

In certain embodiments, the planar contact face 144 of the release member 136 comprises an anti-friction layer for reducing or minimizing friction between the contact faces 144, 156 of the release member 136 and the base member 134. As illustrated in FIGS. 23 to 25, the anti-friction layer comprises a disc 194 attached to the release member 136 and with an outer face 196 which is the planar contact face 144 and having anti-friction properties. In this embodiment, the recesses 192 for receiving the spring loaded ball bearings 188 are formed in the disc 194. In other embodiments, the anti-friction layer comprises a coating. The anti-friction layer may comprise any material that reduces friction between the base member 134 and the release member 136.

The coupling device 100 further comprises a top plate 198 attachable to the collar 146 of the release member 136 and attachable to the equipment 12. As best seen in FIG. 18, the top plate 198 is attached to the collar 146 by fasteners 200, such as screws. The top plate 198 has an opening formed therein.

In certain embodiments (for example as illustrated in FIGS. 18 to 26), when the base member 134 and the release member 136 are coupled together and in the lock position, the release member 136 is rotatable within the pocket 162 whilst maintaining the coupling. In this respect, the perimeter 148 of the plate-like body 138 of the release member 136 is circular in shape, the stop member 166 of the base member 134 is positioned substantially centrally of the planar contact portion 156, and the opening 176 of the release member 136 is positioned substantially centrally of the plate-like body 138, such that the release member 136 can be rotated within the pocket 162 when the stop member 166 is in the lock position. The stop member 166 can be considered to function also as a pivot point in these embodiments.

Figure 27:
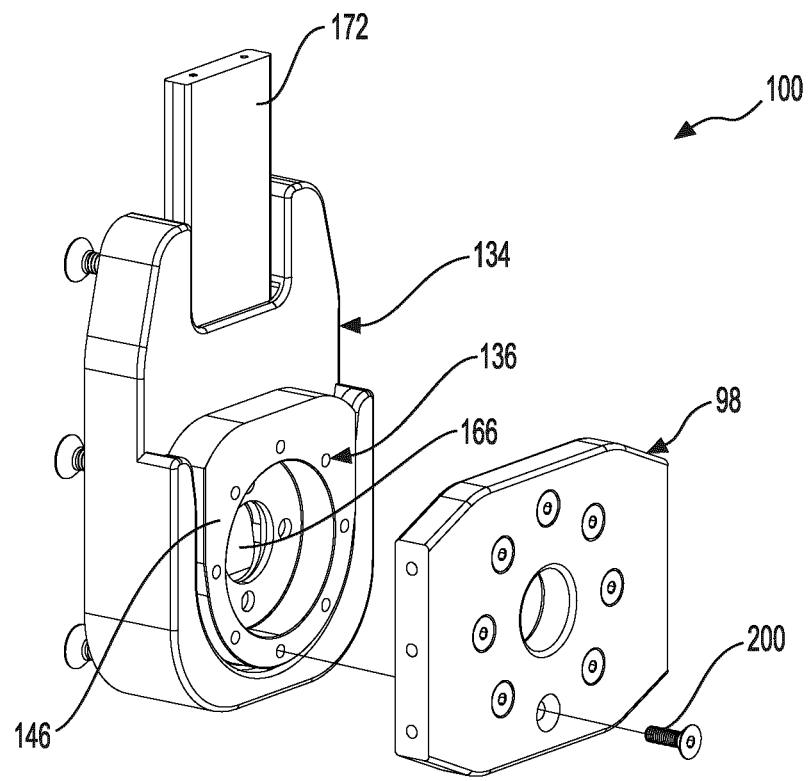
FIG. 27 is a coupling device comprising a base member, a release member, and a top plate, according to certain other embodiments of the present disclosure.
Figure 28:
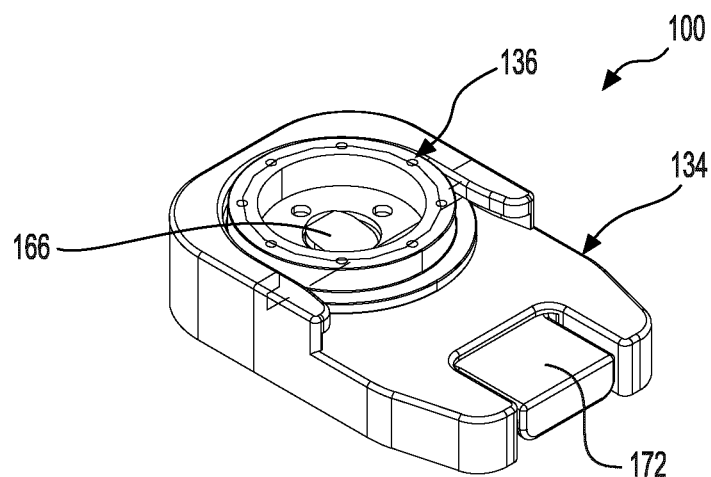
FIG. 28 is the coupling device of FIG. 27, with the top plate removed for clarity, and including a circular member, according to certain embodiments of the present disclosure.

In certain other embodiments (for example as illustrated in FIGS. 27 and 28), when the base member 134 and release member 136 are coupled together and in the lock position, the release member 136 is not rotatable within the pocket 162. In this respect, the perimeter 148 of the plate-like body 138 of the release member 136 has an eccentric shape such that the release member 136 is not rotatable in the pocket 162 of the base member 134. The perimeter 148 of the release member 136 may have a shape which is a multi-faceted geometric form. This embodiment of the coupling device 100 may be used when rotation of the equipment 12 is not required. In certain embodiments, the release member 136 further comprises a circular member 206 which is rotatable within the pocket 162 (FIG. 28).

In certain embodiments, the coupling device 100 is further provided with a damping member 208 (FIG. 26) attachable to the back side 154 of the base member 134 and arranged to be positioned between the base member 134 and the surface in use. The damping member 208 is arranged to absorb vibrations and shocks/reduce energy transmission. In certain embodiments, the damping member 208 is made of any suitable material such as elastomeric materials.

Returning back to the mounting apparatus 10 of FIGS. 1 to 17B, in certain embodiments, it is provided with at least the base member 134 of one or more coupling devices 100. The corresponding release members 136 would be attached to the equipment 12, such as on a base of the equipment 12.

For example, in FIGS. 1-16, the base members 134 of two coupling devices 100 are provided on the platform 46, and attached to the support face 48. The base members 134 of two other coupling devices 100 are provided on the second side 44 of the first arm 24 and the second arm 26 respectively. The coupling devices 100 provided on the first and second arms 24, 26 are narrower than those positioned on the platform 46. One or more of the coupling devices 100 may correspond to the rotatable embodiments described and illustrated in FIGS. 18-26, or the non-rotatable embodiments described and illustrated in FIGS. 27-28.

In FIGS. 17A and 17B, the base member 134 of the coupling device 100 is provided on the distal end of the first arm 24. In FIG. 17B, the base member of another coupling device 100 is provided on the extension arm 92 of the first arm 24. The coupling device 100 on the extension arm 92 may be smaller and/or lighter than the coupling device at the distal end of the first arm 24.

In certain embodiments, there is also provided a securing apparatus 300, attachable to the mounting apparatus (FIGS. 9-16), for supporting the equipment: a base support member 302 for supporting a bottom face of the equipment, a backing support member 304 for supporting a back face of the equipment, and a top restraining member 306 for engaging a top and/or front face of the equipment. One or more coupling devices 100 can be attached to one or more of the base support member 302, the backing support member 304, and the top restraining member 306. Certain embodiments of a suitable securing apparatus, and/or a suitable coupling device, are described in PCT/CA2020/051329 filed Oct. 2, 2020 claiming priority from U.S. 62/909,408 filed Oct. 2, 2019, the contents of which are herein incorporated by reference.

Variations and modifications will occur to those of skill in the art after reviewing this disclosure. The disclosed features may be implemented, in any combination and subcombinations (including multiple dependent combinations and sub-combinations), with one or more other features described herein. The various features described or illustrated above, including any components thereof, may be combined or integrated in other systems. Moreover, certain features may be omitted or not implemented. Examples of changes, substitutions, and alterations are ascertainable by one skilled in the art and could be made without departing from the scope of the information disclosed herein.

It should be appreciated that the invention is not limited to the particular embodiments described and illustrated herein but includes all modifications and variations falling within the scope of the invention as defined in the appended claims.

The invention claimed is:

1. A mounting apparatus for moveably securing equipment to a patient transport system, the mounting apparatus comprising:
    a first arm having a proximal end defining an elongate opening, a distal end and a longitudinal axis, and configured to support equipment; and
    a clamping system attachable to the patient transport system and configured to receive the proximal end of the first arm for removeably attaching the first arm to the patient transport system and for allowing a rotation of the first arm relative to the patient transport system between an upright position and a reclined position, the clamping system comprising:
    a body having:
        a foot portion configured to be attached to the patient transport system,
        a cover portion arranged to be removeably attached to the foot portion, the cover portion defining a first opening and a second opening which overlays over the elongate opening of the first arm, the first opening and the second opening being spaced apart from one another, and
        a slot for receiving the proximal end of the first arm, the slot disposed between the foot and cover portions;
    a pin, insertable through the body and the proximal end of the first arm; and
    a removable pivot pin configured to extend through the elongate opening of the first arm and transverse to the pin when assembled, the removable pin being selectively received in one of the first opening to lock the first arm in the upright position, and the second opening to lock the first arm in the reclined position.

2. The mounting apparatus of claim 1, wherein there is another opening defined in the proximal end of the first arm configured such that the pin is configured to extend therethrough.

3. The mounting apparatus of claim 1, further comprising interengageable elements between a rim of the proximal end of the first arm and a wall inside the body, the wall at least partially defining the slot.

4. The mounting apparatus of claim 3, wherein the interengageable elements comprise teeth and notches, the teeth extending from the rim and the notches being formed in the wall.

5. The mounting apparatus of claim 1, wherein the proximal end is a flat end having two faces and a rim of the proximal end separating the two faces.

6. The mounting apparatus of claim 1, wherein the pin is resiliently biased towards the first arm.

7. The mounting apparatus of claim 1, wherein the first opening and the second opening are defined on a rim of the proximal end of the first arm.

8. The mounting apparatus of claim 1, further comprising a second arm spaced from the first arm, the second arm having a distal end, a proximal end and a longitudinal axis and the first arm being connected to the second arm by a connecting member at respective distal ends of each of the first arm and the second arm.

9. The mounting apparatus of claim 8, further comprising a platform at the distal ends of the first arm and the second arm, the platform having a support face with a support surface plane which is substantially transverse to the longitudinal axis of the first arm and the second arm.

10. The mounting apparatus of claim 9, wherein the platform is positioned distally of the connecting member and connected thereto.

11. The mounting apparatus of claim 9, further comprising at least one transverse reinforcement member extending along at least a portion of the platform, the at least one transverse reinforcement member extending substantially transversely to the connecting member.

12. The mounting apparatus of claim 1, further comprising at least one handle extending from the first arm.

13. The mounting apparatus of claim 1, wherein the patient transport system is a stretcher and the equipment is medical equipment.

14. The mounting apparatus of claim 1, further comprising a base member of a coupling device attached to the first arm, the base member having a front face defining a pocket for releasably receiving a release member of the coupling device, the release member configured to be releasably attached to the equipment.

15. The mounting apparatus of claim 1, further comprising a coupling device attached to the first arm, the coupling device comprising a base member, a release member, and a stop member wherein:

the base member has a front face including a contact portion for contacting a contact face of the release member of the coupling device;

the release member comprises a body, at least a portion of the body being configured to be received in a pocket on the front face of the base member when the base member and the release member are in a coupled position, the pocket having an open access end through which the release member is configured to be slidingly inserted and removed; and the stop member is moveable, by an actuator, between a lock position in which the stop member interengages with the release member to prevent removal of the release member from the pocket of the base member, and a release position in which the release member is configured to be separated from the base member.

16. The mounting apparatus of claim 15, wherein the base member has a shoulder extending around the contact portion to define the pocket for receiving the release member, the shoulder engageable with a portion of a flange of the release member when the release member is positioned on the base member.

\* \* \* \* \*